United States Patent [19]

Varney et al.

[11] Patent Number: 5,625,061

[45] Date of Patent: Apr. 29, 1997

[54] COMPOUNDS USEFUL IN PREPARING ANTIPROLIFERATIVE AGENTS AND GARFT INHIBITORS

[75] Inventors: Michael D. Varney, Carlsbad; William H. Romines, San Diego; Cynthia L. Palmer, La Mesa, all of Calif.

[73] Assignee: Agouron Pharmaceuticals, Inc., La Jolla, Calif.

[21] Appl. No.: 477,633

[22] Filed: Jun. 7, 1995

Related U.S. Application Data

[60] Division of Ser. No. 282,293, Jul. 28, 1994, which is a continuation-in-part of Ser. No. 10,861, Jan. 29, 1993.

[51] Int. Cl.$^6$ .................... C07D 403/08; C07D 403/10; C07D 403/12
[52] U.S. Cl. .................... 544/1; 544/48; 544/105
[58] Field of Search .................... 544/48, 255, 1, 544/105

[56] References Cited

U.S. PATENT DOCUMENTS

| | | | |
|---|---|---|---|
| 4,123,550 | 10/1978 | Untch et al. | 544/279 |
| 4,684,653 | 8/1987 | Taylor et al. | 514/258 |
| 4,686,223 | 8/1987 | Cohnen et al. | 544/279 |
| 4,831,037 | 5/1989 | Taylor et al. | 514/258 |
| 4,845,216 | 7/1989 | Taylor et al. | 514/258 |
| 4,871,743 | 10/1989 | Taylor et al. | 514/258 |
| 4,871,746 | 10/1989 | Taylor et al. | 514/258 |
| 4,880,812 | 11/1989 | Kelley | 544/279 |
| 4,882,333 | 11/1989 | Shih et al. | 514/258 |
| 4,882,334 | 11/1989 | Shih et al. | 514/258 |
| 4,883,799 | 11/1989 | Taylor et al. | 514/258 |
| 4,889,859 | 12/1989 | Taylor et al. | 514/258 |
| 4,895,946 | 1/1990 | Taylor et al. | 514/258 |
| 4,920,125 | 4/1990 | Taylor et al. | 514/258 |
| 4,921,836 | 5/1990 | Bigham et al. | 514/258 |
| 4,927,828 | 5/1990 | Taylor et al. | 514/258 |
| 4,971,973 | 11/1990 | Bigham et al. | 514/258 |
| 4,988,813 | 1/1991 | Taylor et al. | 514/258 |
| 5,013,738 | 5/1991 | Taylor et al. | 514/258 |
| 5,026,851 | 6/1991 | Taylor et al. | 514/258 |
| 5,217,974 | 6/1993 | Grindey et al. | 514/258 |
| 5,223,503 | 6/1993 | Gossett et al. | 514/258 |

FOREIGN PATENT DOCUMENTS

| | | |
|---|---|---|
| 268377 | 5/1988 | European Pat. Off. . |
| 325343 | 7/1989 | European Pat. Off. . |
| 341837 | 11/1989 | European Pat. Off. . |
| 438261 | 7/1991 | European Pat. Off. . |
| 593286 | 4/1994 | European Pat. Off. . |
| WO86/05181 | 9/1986 | WIPO . |
| WO92/05153 | 4/1992 | WIPO . |
| WO94/13295 | 6/1994 | WIPO . |

OTHER PUBLICATIONS

Moran, "Folate antimetabolites inhibitory to de novo purine synthesis," New Drugs, Concepts and Results in Cancer Chemotherapy, Muggia (ed.), Kluwer Academic Publishers, Boston (1992), 65–87.

Young et al., "An Antibody Probe to Determine the Native Species of Glycinamide Ribonucleotide Transformylase in Chicken Liver," Biochemistry, vol. 23 (1984), 3979–3986.

Morrison, "Kinetics of the Reversible Inhibition of Enzyme–Catalysed Reactions by Tight–Binding Inhibitors," Biochem. Biophys. Acta, 185 (1969), 269–286.

Mosmann, "Rapid Colorimetric Assay for Cellular Growth and Survival . . . " J. Immunol. Methods, vol. 65 (1983), 55–63.

Sako et al., "New and Facile Synthesis of 5,6,7,8–Tetrahydro–5–deaza–5–thiapterins . . . . " Chem. Pharm. Bull., vol. 42, No. 4 (1994), 806–810.

Antony, "The Biological Chemistry of Folate Receptors," Blood, The Journal of the American Society of Hematology, vol. 79, No. 11 (1992), 2807–2820.

Pizzorno et al., "5,10–Dideazatetrahydrofolic Acid (DDATHF) Transport in CCRF–CEM and MA104 Cell Lines," The Journal of Biological Chemistry, vol. 268, No. 2 (1993), 1017–1023.

Alati et al., "Evaluation of the Mechanism(s) of Inhibition of the Toxicity, but not the Antitumor Activity of Lometrexol . . . . " Proceedings of the Am. Assoc. for Cancer Res., Abstract 2432, vol. 33 (1992), 407.

Shih et al., "Synthesis and Biological Activity of Acyclic Analogues of 5,10–Dideaza–5,6,7,8–tetrahydrofolic Acid," J. Med. Chem., vol. 35 (1992), 1109–1116.

Nemec et al., "The Synthesis of 4–Substituted 2–Thiophenecarboxylic Acids," Collection Czechoslov. Chem. Commun., vol. 39 (1974), 3527–3531.

Taylor et al., "Convergent and Efficient Palladium–Efected Synthesis of . . . (DDATHF)," J. Org. Chem., vol. 54, No. 15 (1989), 3618–3624.

(List continued on next page.)

Primary Examiner—Matthew V. Grumbling
Attorney, Agent, or Firm—Finnegan, Henderson Farabow, Garrett & Dunner, L.L.P.

[57] ABSTRACT

Compounds of the invention include those of the following formula:

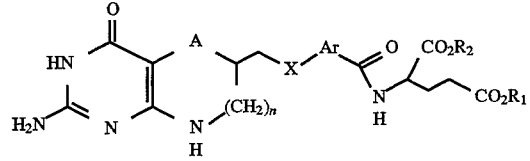

In this formula, A is oxygen, sulfur or selenium; X' is a substituted or unsubstituted $C_1$–$C_3$ alkyl group, a substituted or unsubstituted $C_2$–$C_3$ alkenyl group, a substituted or unsubstituted $C_2$–$C_3$ alkynyl group, a substituted or unsubstituted amino group, sulfur or oxygen; Y is oxygen, sulfur or NH; B is hydrogen or a halogen; C is hydrogen, a halogen or a substituted or unsubstituted $C_1$–$C_6$ alkyl group; and $R_6$ is hydrogen or a moiety that forms with the attached $CO_2$ a readily hydrolyzable ester group.

8 Claims, No Drawings

OTHER PUBLICATIONS

Habeck et al., "A Novel Class of Monoglutamated Antifolates Exhibits Tight–binding Inhibition of Human Glycinamide Ribonucleotide Formyltransferase and Potent Activity Against Solid Tumors," Cancer Research, vol. 54 (Feb. 5, 1994), 1021–1026.

Henrie II et al., "Preparation of 2–Amino–4(3H)–oxopyrimido[5,4–b][1,4]–thiazines . . .," J. Med. Chem., vol. 26, No. 4 (1993), 559–563.

Okafar, "Studies in the Heterocyclic Series XVIII . . . ," J. Heterocyclic Chem., vol. 17, No. 7 (1980), 1587–1592.

Alley et al., "Feasibility of Drug Screening with Panels of Human Tumor Cell Lines Using Microculture Tetrazolium Assay," Cancer Res., vol. 48 (1988), 589–601.

Cleland, "The Kinetics of Enzyme–Catalyzed Reactions with Two or More Substrates or Products," Biochem. Biophys. Acta, vol. 67 (1963), 173–187.

Casarrubio et al., "On the Syntheses of Thiophene Analogs of Practolol and 'Reversed' Practolol," J. Heterocyclic Chem., vol. 20, No. 6, Nov.–Dec. 1983, 1557–1560.

COMPOUNDS USEFUL IN PREPARING ANTIPROLIFERATIVE AGENTS AND GARFT INHIBITORS

This is a divisional of Ser. No. 08/282,293, filed Jul. 28, 1994, which is a continuation-in-part of Ser. No. 08/010,861, filed Jan. 29, 1993.

BACKGROUND OF THE INVENTION

The present invention relates to compounds defined below that inhibit the enzyme glycinamide ribonucleotide formyl transferase (GARFT). The invention also relates to intermediates for preparing these compounds, to pharmaceutical compositions containing the compounds, to their use to inhibit GARFT and to their use to inhibit the growth or proliferation of the cells of higher organisms or microorganisms such as bacteria, yeast and fungi. The compounds have antitumor, antiinflammatory, antipsoriatic and/or immunosuppressive activity. The invention also relates to the preparation of these compounds.

The large class of antiproliferative agents includes antimetabolite compounds. A particular subclass of antimetabolites known as antifolates or antifoles are antagonists of the vitamin folic acid. Typically, antifolates closely resemble the structure of folic acid and incorporate the characteristic P-benzoyl glutamate moiety of folic acid. The glutamate moiety of folic acid takes on a double negative charge at physiological pH. Therefore, this compound and its analogs have an active energy driven transport system to cross the cell membrane and exert a metabolic effect.

Glycinamide ribonucleotide formyl transferase (GARFT) is a folate dependent enzyme in the de novo purine biosynthesis pathway. This pathway is critical to cell division and proliferation. Shutting down this pathway is known to have an antiproliferative effect, in particular, an antitumor effect. Thus, a number of folate analogs have been synthesized and studied for their ability to inhibit GARFT. A prototypical specific tight binding inhibitor of GARFT, 5,10-dideazatetrahydrofolic acid, has been reported to show antitumor activity. See F. M. Muggia, "Folate antimetabolites inhibitor to de novo purine synthesis," *New Drugs, Concepts and Results in Cancer Chemotherapy*, Kluwer Academic Publishers, Boston (1992), 65–87.

SUMMARY OF THE INVENTION

The present invention relates to compounds defined below, which contain a glutamic acid or ester moiety. These compounds are effective in inhibiting the enzyme glycinamide ribonucleotide formyl transferase (GARFT) and the growth and proliferation of cells of higher organisms and of microorganisms such as bacteria, yeast and fungi. The invention further relates to pharmaceutical compositions containing these compounds or suitable salts thereof, and to the use of these compounds as inhibitors of GARFT.

As indicated above, compounds of the invention possess antiproliferative activity, a property which can express itself in the form of antitumor activity. A compound of the invention can be active per se, or as a precursor converted in vivo to an active compound. Preferred compounds of the invention are especially active in inhibiting the enzyme GARFT. Particularly preferred compounds are active in inhibiting the growth of the L1210 cell line, a mouse leukemia cell line that can be grown in tissue culture. Compounds of the invention can also be active in inhibiting the growth of bacteria such as *Escherichia coli* gram-negative bacteria which can be grown in culture.

The compounds according to the invention, as well as the pharmaceutically acceptable salts thereof, may be incorporated into convenient dosage forms, such as capsules, tablets, or injectable preparations. Solid or liquid pharmaceutically acceptable carriers, diluents or excipients may also be employed.

Solid carriers include starch, lactose, calcium sulphate dihydrate, terra alba, sucrose, talc, gelatin, agar, pectin, acacia, magnesium stearate and stearic acid. Liquid carriers include syrup, peanut oil, olive oil, saline solution and water.

The carrier or diluent may include any prolonged-release material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a nonaqueous or aqueous liquid suspension.

The pharmaceutical preparations are prepared following conventional techniques of the pharmaceutical chemist involving steps such as mixing, granulation, and compressing when necessary for tablet forms, or mixing, filling and dissolving the ingredients as appropriate to give the desired products for oral, parenteral, topical, intravaginal, intranasal, intrabronchial, intraocular, intraaural and rectal administration.

The compositions of the invention may further comprise one or more other pharmaceutically active compounds. For example, one of the following antitumor agent may be included in the composition: mitotic inhibitors (e.g., vinblastine); alkylating agents; dihydrofolate reductase inhibitors or TS inhibitors; antimetabolites (for example, 5-fluorouracil, cytosinerabinoside); intercalating antibiotics (for example, adriamycin, bleomycin); enzymes (for example, asparaginase); topoisomerase inhibitors (for example, etoposide); and biological response modifiers (for example, interferon). The compositions of the invention may also comprise another GARFT inhibitor or antiproliferative agent, such as a compound described in commonly assigned International Application No. PCT/US93/11795, filed Dec. 10, 1993, or International Publication No. WO 92/05153, published Apr. 2, 1992, the disclosures of which are incorporated by reference herein. The compositions of the invention may also comprise one or more antibacterial, antifungal, antiparasitic, antiviral, antipsoriatic or anticoccidial agent. Exemplary antibacterial agents include: sulfonamides, such as sulfamethoxazole, sulfadiazine, sulfameter or sulfadoxine; dihydrofolic reductase inhibitors, such as trimethoprim, bromodiaprim, or trimetrexate; penicillins; cephalosporins; and the quinolone carboxylic acids and their fused isothiazolo analogs.

Another aspect of the invention relates to a therapeutic method of inhibiting the growth and proliferation of cells of higher organisms or microorganisms, which comprises administering to a host an effective amount or quantity of a compound according to the present invention. The compounds of the invention are particularly useful in the treatment of mammalian hosts, such as human hosts, and in the treatment of avian hosts. A particularly preferred therapeutic process comprises administering to a host an amount of a compound according to the present invention effective to inhibit GARFT.

Many of the antiproliferative compounds described herein and their pharmaceutically acceptable salts thereof can be employed in the therapeutic process of the invention. The compounds may be administered in the form of a pharmaceutically acceptable composition comprising a diluent or carrier as described above.

A dose of a composition contains at least an effective quantity of the active compound and preferably is made up of one or more pharmaceutical dosage units. An "effective quantity" means a quantity sufficient to inhibit the folate metabolic pathways and derive the beneficial effects therefrom, e.g., through administration of one or more of the pharmaceutical dosage units.

An exemplary daily dose for a vertebrate host comprises an amount up to one gram of active compound per kilogram of the host, preferably one-half of a gram, more preferably 100 milligrams, and most preferably, about 50 milligrams or less, per kilogram of the host weight. The selected dose may be administered to a warmblooded animal or mammal, for example, a human patient in need of treatment mediated by folate metabolic pathways inhibition, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

The compounds according to the present invention produce any one or more of an antiproliferative effect, an antibacterial effect, an antiparasitic effect, an antiviral effect, an antipsoriatic effect, an antiprotozoal effect, an anticoccidial effect, an antiinflammatory effect, an immunosuppressive effect and an antifungal effect. The compounds are especially useful in producing an antitumor effect in a vertebrate host harboring a tumor.

DETAILED DESCRIPTION OF THE INVENTION

The present invention relates to antiproliferative compounds capable of inhibiting GARFT and of the formula I

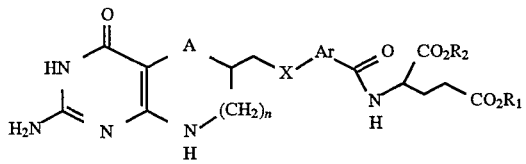

wherein:

n an integer from 0 to 2;

A is sulfur, $CH_2$, oxygen, NH or selenium, provided that when n is 0, A is not $CH_2$, and when n 1, A is not $CH_2$ or NH;

X is at least one substituted or unsubstituted $C_1$–$C_3$ alkyl, substituted or unsubstituted $C_2$–$C_3$ alkenyl group, substituted or unsubstituted $C_2$–$C_3$ alkynyl group, substituted or unsubstituted amino group, sulfur or oxygen;

Ar is a substituted or unsubstituted monocyclid carbocyclic or heterocyclic ring, or a fused or nonfused polycyclic carbocyclic or heterocyclic ring system; and $R_1$ and $R_2$ are each independently hydrogen or a moiety that forms, together with the attached $CO_2$, a readily hydrolyzable ester group. The invention also relates to pharmaceutically acceptable salts of compounds of the formula I.

Preferred moieties for $R_1$ and $R_2$ are hydrogen, $C_1$–$C_6$ alkyl, hydroxyalkyl, alkylaryl and aralkyl. Particularly preferred moieties are hydrogen and $C_2$ alkyl.

Where X or Ar is substituted, preferred substituents for X and Ar include $C_1$–$C_6$ alkyl, $C_2$–$C_6$ alkenyl, $C_2$–$C_6$ alkynyl, acyl, halogen, amino, hydroxyl, nitro, mercapto, monocyclic carbocyclic or heterocyclic rings, fused or nonfused polycyclic carbocyclic or heterocyclic ring systems, hydroxy $C_1$–$C_6$ alkyl and $C_1$–$C_6$ alkoxy $C_1$–$C_6$ alkyl.

It is particularly preferred that A be sulfur and that Ar be phenyl.

Preferred compounds of the invention include compounds of the subgeneric formula II:

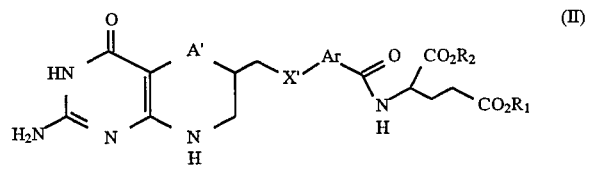

wherein:

A' is sulfur or selenium;

X' is $CH_2$, sulfur, oxygen or NH;

Ar is as defined in formula I; and $R_1$ and $R_2$ are as defined in formula I; and pharmaceutically acceptable salts thereof.

Preferred moieties for $R_1$ and $R_2$ are hydrogen, $C_1$–$C_6$ alkyl, hydroxyalkyl, alkylaryl and aralkyl. Particularly preferred moieties are hydrogen and $C_2$ alkyl.

A' is preferably sulfur, X' is preferably $CH_2$ and Ar is preferably phenyl.

Although the compounds are depicted in the formulae I and II in the 4-oxo form and are referred to as such throughout this description, the oxo group exists in tautomeric equilibrium with the corresponding 4-hydroxy group and it will be understood that in each case the tautomeric hydroxyl form is also indicated.

The compounds of formulae I and II in which each of $R_1$ and $R_2$ is hydrogen are active anti-tumor and antiproliferative compounds. The compounds of formula I wherein $R_1$ and $R_2$ are moieties which form with the attached $CO_2$ a readily hydrolyzable ester group, preferably an ethyl group, are novel intermediates for forming the free glutamic acid forms of the compounds and can also be hydrolyzed in vivo and thus act as prodrugs.

The invention also includes pharmaceutically acceptable salts, including, for example, alkaline metal, alkaline earth metal, other non-toxic metals, ammonium and substituted ammonium salts of the glutamic acid embodiments of the invention such as, but not limited to, the sodium, potassium, lithium, calcium, magnesium, aluminum, zinc, ammonium, trimethyl ammonium, triethyl ammonium, pyridinium and substituted pyridinium salts.

Compounds of the formula I can be prepared by reacting a compound of the formula III:

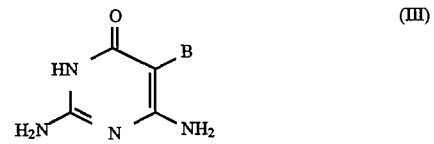

wherein:

B is a halogen, preferably bromo, with a compound of the formula IV:

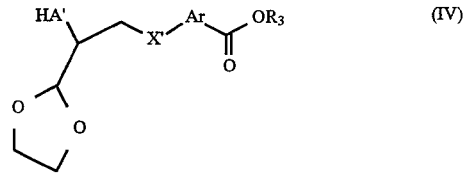

wherein X', A', and Ar are as defined in formula II and $R_3$ is hydrogen or a straight, branched or cyclic $C_1$ to $C_6$ alkyl group optionally carrying one or more halogen, hydroxyl or amino groups; in the presence of base other than the compound of formula III, preferably a non-nucleophilic auxiliary base, in a solvent in which at least one of the reactants is at least partially soluble under conditions sufficient to obtain the compound of formula V:

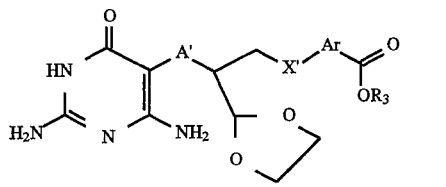

(V)

wherein A', X', and Ar are defined as in formula II, and $R_3$ is as defined in formula IV.

The reaction of the compound of formula III with the compound of formula IV is preferably carried out in a suitable solvent in which at least one or both reactants are soluble at the reaction temperature. The solvent and the reaction environment are preferably purged of oxygen prior to introduction of the reactants by bubbling an inert gas, such as argon or nitrogen, through the solvent. Bubbling of the inert gas is preferably continued until the reaction has gone to completion and been quenched, such as by pouring into water. A preferred solvent is a dipolar aprotic solvent such as, e.g., dimethylsulfoxide, N,N-dimethylformamide, N,N-dimethylacetamide or N-methyl-2-pyrrolidinone.

The basic medium for the reaction of the compounds of formulae III and IV is preferably provided via a non-nucleophilic auxiliary base, which is defined as a base capable of neutralizing hydrogen halide gas generated by the substitution reaction. The base is preferably an alkali or alkali earth metal carbonate or a trialkylamine, such as, e.g., trimethylamine, triethylamine or diisopropylethylamine.

The preferred method for conducting the reaction of compounds of the formulae IV and III is to suspend the compound of formula III, preferably 5-bromo-2,6-diamino-4(3H)-oxo-pyrimidine, in the solvent. The compound of the formula IV and the auxiliary base are then added sequentially.

The reaction vessel is then immersed in an oil bath which has been heated to the appropriate temperature (20°–200°, preferably 70°–120° C). The reaction mixture can be stirred at this temperature for the requisite length of time (usually 30–330 minutes), followed by cooling to room temperature and pouring into water. The product, the compound of formula V, can then be isolated by filtration or extraction with an organic solvent and purified either by recrystallization or by chromatography.

The compound of formula V can be reacted with an acid, preferably hydrochloric acid, in a suitable solvent, preferably tetrahydrofuran, under conditions sufficient, preferably reflux, to obtain a compound of the formula VI:

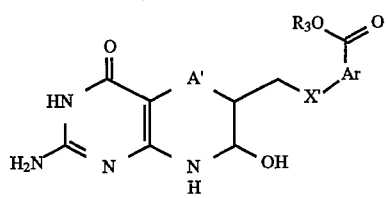

(VI)

wherein A', X' and Ar are defined as in formula II, and $R_3$ is as defined in formula IV.

Compound VI is then reduced, preferably with sodium cyanoborohydride, to obtain a compound of the formula VII:

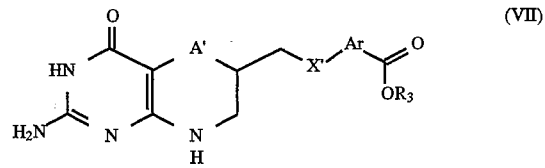

(VII)

wherein A', X' and Ar are defined as in formula II and $R_3$ is as defined in formula IV.

The compound of formula VII is hydrolyzed, under basic conditions, to form a compound of the formula VIII:

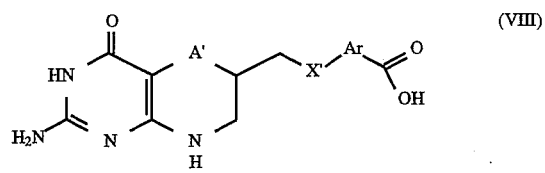

(VIII)

wherein A', X' and Ar are defined as in formula II. Where, in the compound of formula VII, $R_3$ is hydrogen, then this reaction step is not necessary, and the compound of formula VII can be peptide coupled, as described immediately below.

The compound of formula VIII (or the compound of formula VII, wherein $R_3$ is hydrogen), which is in free carboxylic acid form, can be peptide coupled, by means well known to those skilled in the art, with a glutamic acid diester hydrochloride, to form a diester of the formula IX:

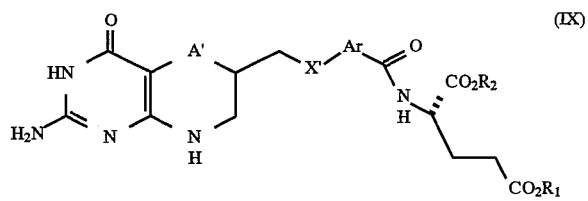

(IX)

wherein A', X', Ar, $R_1$ and $R_2$ are as defined in formula II, provided that neither $R_1$ nor $R_2$ is hydrogen. Finally, if desired, the compound of formula IX can be hydrolyzed to the free glutamic acid form depicted in formula II ($R_1$ and $R_2$=H).

Preferred examples of compounds of the formula II include:

(2-[4-[2-(2-Amino-4-oxo-4,6,7,8-tetrahydro-3H-pyrimido[5,4-6][1,4]thiazin-6-yl]-ethyl]-benzoylamino]-pentanedioic acid) diethyl ester; and (2-[4-[2-(2-Amino-4-oxo-4,6,7,8-tetrahydro-3H-pyrimido [5,4-6][1,4]thiazin-6-yl]-ethyl]benzoylamino]-pentanedioic acid). The L-form of these compounds is preferred.

The present invention relates to antiproliferative compounds of formula XI:

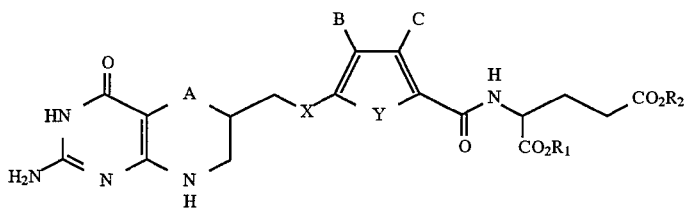

(XI)

wherein:

A is O, S or Se;

X is a substituted or unsubstituted $C_1$–$C_3$ alkyl group, a substituted or unsubstituted $C_2$–$C_3$ alkenyl group, a substituted or unsubstituted $C_2$–$C_3$ alkynyl group, a substituted or unsubstituted amino group, sulfur or oxygen;

Y is O, S or NH;

B is hydrogen or a halogen (F, Cl, Br or I);

C is hydrogen, a halogen or a substituted or unsubstituted $C_1$–$C_6$ alkyl group; and $R_1$ and $R_2$ are independently hydrogen or a moiety that forms, together with the attached $CO_2$, a readily hydrolyzable ester group, such as a $C_1$–$C_6$ alkyl. The invention further relates to pharmaceutically acceptable salts of the compounds of the formula XI. The invention also relates to intermediates for making such compounds.

Although the compounds of the formula XI are shown in the 4-oxo form and are referred to as such in this description, the oxo group exists in tautomeric equilibrium with the corresponding 4-hydroxy group. It will therefore be understood that the term the compounds of the invention include the structurally depicted 4-oxo and the tautomeric 4-hydroxy forms. Thus, the invention also relates to pharmaceutically acceptable salts of the 4-hydroxy tautomers of the compounds depicted by formula XI.

Where X or C is substituted, preferred substituents include $C_1$–$C_6$ alkyl, $C_2$–$C_6$ alkenyl, $C_2$–$C_6$ alkynyl, acyl, halogen, amino, hydroxyl, nitro, mercapto, monocyclic carbocycle, monocyclic heterocycle, fused and nonfused polycyclic carbocycle, fused and nonfused polycyclic heterocycle, hydroxy $C_1$–$C_6$ alkyl and $C_1$–$C_6$ alkoxy $C_1$–$C_6$ alkyl.

Preferably, X is $CH_2$, $CH_2CH_2$, NH, oxygen, sulfur, $CH(CH_2OH)$ or $NCH_3$. Y is preferably S or O. Preferably, B is hydrogen. C is preferably hydrogen or $CH_3$. Preferably, $R_1$ and $R_2$ are independently selected from hydrogen, $C_1$–$C_6$ alkyl, hydroxyalkyl, alkylaryl and arylalkyl, most preferably, from hydrogen and $C_1$–$C_2$ alkyl. It is particularly preferred that A and Y are each sulfur and X is $CH_2$.

The compounds of the formula XI are useful as GARFT inhibitors. The compounds of formula XI in which $R_1$ and $R_2$ are each hydrogen are especially active antitumor or antiproliferative agents. The compounds of formula XI wherein $R_1$ and $R_2$ are each a moiety that forms with the attached $CO_2$ a readily hydrolyzable ester group, preferably an ethyl group, are useful intermediates for forming the free glutamic acid forms of the compounds and can also be hydrolyzed in vivo and thus act as prodrugs.

The pharmaceutically acceptable salts of the invention include, for example, alkaline metal, alkaline earth metal, other non-toxic metals, and ammonium and substituted ammonium salts of the glutamic acid compounds of the invention. Exemplary salts include sodium, potassium, lithium, calcium, magnesium, pyridinium and substituted pyridinium salts of the free acid compounds.

The compounds of the formula XI can be prepared as follows. A useful starting material for preparing compounds of the formula XI wherein X is $CH_2$ is a compound of formula XII:

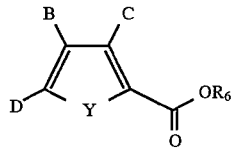

(XII)

wherein B, C and Y are as defined above for formula XI; D is Cl, Br or I; and $R_6$ is a hydrogen or a moiety that forms with the attached $CO_2$ a readily hydrolyzable ester group. Preferably, D is bromo or iodo. Preferably, $R_6$ is hydrogen, $C_1$–$C_6$ alkyl, hydroxyalkyl, alkylaryl or arylalkyl, more preferably, hydrogen or $C_1$–$C_2$ alkyl.

The compound of the formula XII is reacted with a compound of formula XIII:

(XIII)

wherein $R_3$ is a substituted or unsubstituted $C_1$–$C_6$ alkyl group, or a trisubstituted silyl group. Preferably, $R_3$ is $CH_2OH$ or trimethylsilyl.

The reaction of the compounds of the formulae XII and XIII is carried out in the presence of a suitable transition-metal catalyst, preferably palladium or nickel, a non-nucleophilic auxiliary base, preferably a substituted amine, in a solvent in which at least one of the reactants is at least partially soluble under conditions sufficient to obtain a compound of formula XIV:

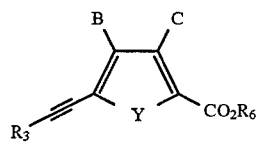

(XIV)

wherein B, C and Y are as defined above for formula XI; $R_6$ is as defined above for formula XII; and $R_3$ is as defined above for formula XIII.

When $R_3$ is a trisubstituted silyl group, the silyl group is preferably removed with a nucleophilic base, such as methanolic or ethanolic potassium carbonate, or a fluoride salt, such as potassium fluoride, cesium fluoride or tetrabutylammonium fluoride, in a solvent in which at least one of the reactants is at least partially soluble (e.g., methanol, dimethylformamide, ethanol, dimethylacetamide, dimethylsulfoxide or isopropanol) to give a compound of formula XV:

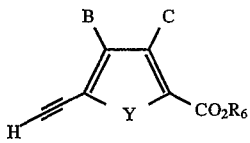 (XV)

wherein B, C and Y are as defined above for formula XI; and $R_6$ is as defined above for formula XII.

The compound of formula XV is reacted with an electrophile, preferably an N-protected glycinal, more preferably N-t-butoxycarbonylglycinal or bis-N-t-butoxycarbonylglycinal, under basic conditions using a non-nucleophilic base, preferably lithium bis-trimethyl-silylamide, potassium bis-trimethyl-silylamide, sodium bis-trimethylsilylamide or lithium diisopropylamide, at a low temperature, preferably from −90° C. to 25° C., in a suitable solvent in which one of the reactants is at least partially soluble, preferably tetrahydrofuran, diethyl ether or dioxane, to give a compound of formula XVI:

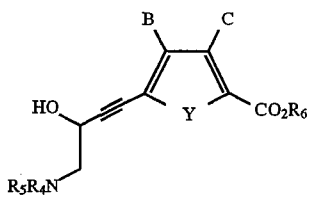 (XVI)

wherein B, C and Y are as defined above for formula XI; $R_6$ is as defined above for formula II; and $R_4$ and $R_5$ are each independently hydrogen or a readily removable nitrogen-protecting group. $R_4$ and $R_5$ are preferably hydrogen, t-butoxycarbonyl, benzyloxycarbonyl or benzyl.

The compound of the formula XVI is then reduced, preferably with hydrogen gas in the presence of a suitable metal catalyst, to obtain a compound of the formula XVII:

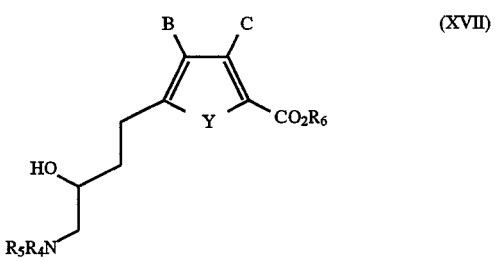 (XVII)

wherein B, C and Y are as defined above for formula XI; $R_6$ is as defined above for formula XII; and $R_4$ and $R_5$ are as defined above for formula XVI.

The compound of the formula XVII is then reacted with an acylating or sulfonylating agent, preferably methanesulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is displaced with a suitable nucleophile, preferably a thioacid salt, more preferably potassium thioacetate, to obtain a compound of formula XVIII:

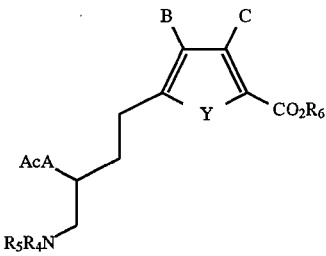 (XVIII)

wherein A, B, C and Y are as defined above for formula XI; $R_6$ is as defined above for formula XII; $R_4$ and $R_5$ are as defined above for formula XVI; and Ac is an acyl group, preferably acetyl.

Alternatively, the compound of formula XVII is converted to the compound of formula XVIII in one chemical operation using triphenylphosphine, diethyl or dimethyl aza-dicarboxylate, and an acidic nucleophile, preferably thioacetic acid, in a suitable solvent.

The compound of the formula XVIII is treated with a nucleophilic base, preferably potassium carbonate, sodium carbonate, sodium hyroxide or potassium hydroxide, in an alcoholic solvent, preferably methanol, ethanol or isopropanol, in the presence of an alkylating agent, preferably dimethyl or diethyl chloromalonate, to obtain a compound of formula XIX:

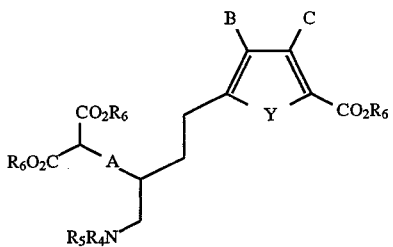 (XIX)

wherein A, B, C and Y are as defined above for formula XI; $R_6$ is as defined above for formula XII; and $R_4$ and $R_5$ are as defined above for formula XVI.

The compound of the formula XIX is treated under conditions suitable to remove either or both of the $R_4$ and $R_5$ protecting groups to produce a compound of the formula XX:

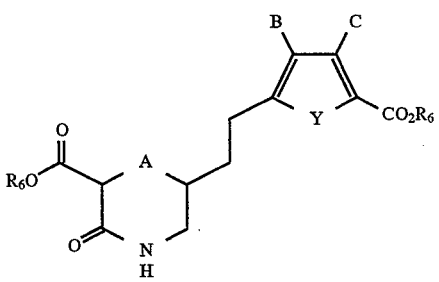 (XX)

wherein A, B, C and Y are as defined above for formula XI; and $R_6$ is as defined above for formula XII. Where t-butoxycarbonyl (t-BOC) is a protecting group, the conditions for removal of this group are preferably treatment with trifluoroacetic acid followed by neutralization to produce the compound of the formula XX.

The compound of the formula XX is reacted with an alkylating agent, preferably trimethyl or triethyl oxonium tetrafluoroborate, in a suitable solvent, preferably dichloromethane, to form an intermediate lactim ether. The intermediate lactim ether is reacted with guanidine in an alcoholic solvent, preferably methanol, ethanol or isopropanol, to form a compound of formula XXI:

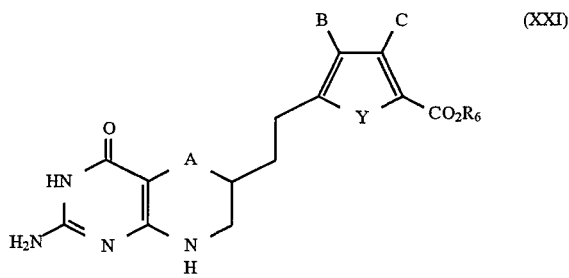

wherein A, B, C and Y are as defined above for formula XI; and $R_6$ is defined above for formula XII.

Alternatively, the compound of the formula XX converted to the compound of the formula XXI by reacting the compound of the formula XX with a thiolating agent, preferably $P_2S_5$ or 2,4-bis(4-methoxyphenyl)-1,3-dithia-2, 4-diphosphetane-2,4-disulfide, to form the thiolactam intermediate. This can then be alkylated with an alkylating agent, preferably methyl iodide or trimethyl or triethyl oxonium tetrafluoroborate, and then with guanidine in an alcoholic solvent, preferably methanol, ethanol or isopropanol, to obtain the compound of the formula XXI.

The compound of the formula XXI is hydrolyzed under basic conditions to form a compound of formula XXII:

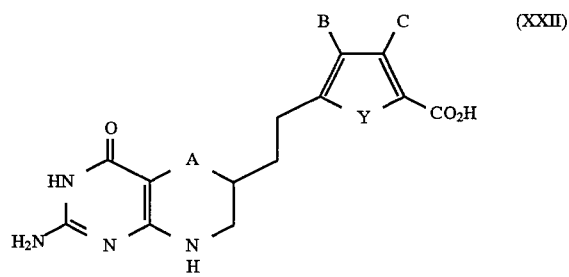

wherein A, B, C and Y are as defined above for formula XI. Where $R_6$ is hydrogen in the compound of the formula XXI, then the hydrolyzation reaction is not necessary, and the compound of the formula XXI is peptide coupled as described below.

The compound of the formula XXII (or the compound of the formula XXI where $R_6$ is hydrogen), which is in the free carboxylic acid form, can be peptide coupled, by means well known to those skilled in the art, with a glutamic acid diester hydrochloride to form a diester of the formula XXIII:

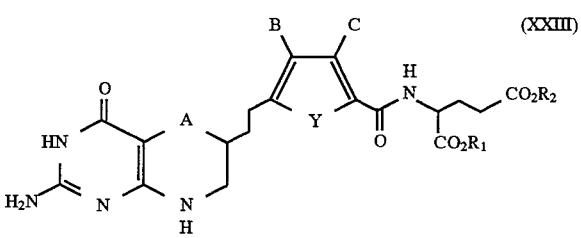

wherein A, B, C and Y are as defined above for formula XI; and $R_1$ and $R_2$ are each independently a moiety that forms with the attached $CO_2$ a readily hydrolyzable ester group, such as a $C_1-C_6$ alkyl, hydroxyalkyl, alkylaryl or arylalkyl.

Finally, if desired, the compound of the formula XXIII is hydrolyzed to the free glutamic acid form of formula XI ($R_1$ and $R_2$ are each H).

Compounds of the formula XI wherein X is other than $CH_2$ can be prepared using an olefin of the formula XXIV:

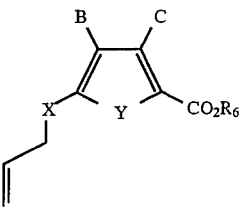

wherein B, C and Y are as defined above for formula XI, X is as defined above for formula XI except that X is other than CH2, and $R_6$ is as defined above for formula XII.

Where X is sulfur, oxygen, or a substituted or unsubstituted amino, the compound of the formula XXIV is prepared by alkylation of a compound of formula XXV:

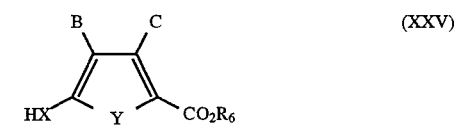

wherein B, C and Y are as defined above for formula XI; X is sulfur, oxygen, or a substituted or unsubstituted amino; and $R_6$ is as defined above for formula XII. The alkylation can be accomplished using an allylhalide, preferably allylbromide, in the presence of a non-nucleophilic base, preferably triethylamine or diisopropylethylamine, to obtain the compound of the formula XXIV.

Where X is a substituted or unsubstituted $C_1-C_2$ alkyl other than $CH_2$, a substituted or unsubstituted $C2-C_3$ alkenyl or a substituted or unsubstituted $C2-C_3$ alkynyl, the compound of the formula XXIV is prepared by olefination of an aldehyde of formula XXVI:

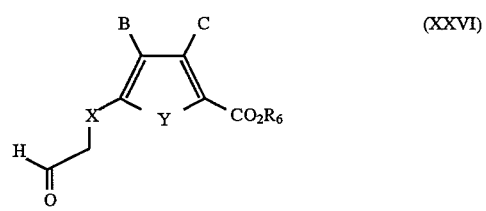

wherein B, C and Y are as defined above for formula XI; and X is a substituted or unsubstituted $C_1-C_2$ alkyl other than CH2, a substituted or unsubstituted $C2-C_3$ alkenyl or a substituted or unsubstituted $C2-C_3$ alkynyl. The aldehyde of the formula XXVI can be prepared in a manner analogous to that described by Chuan Shih et al., *Journal of Medicinal Chemistry*, vol. 35 (1992), 1109–1116.The olefination of the aldehyde can be accomplished using a methylene transfer agent, preferably methylene-triphenylphosphorane.

The compound of the formula XXIV is reacted with a dihydroxylating agent, preferably osmium tetroxide, in the presence of a suitable oxidizing agent, preferably N-methylmorpholine-N-oxide, to obtain a compound of the formula XXVII:

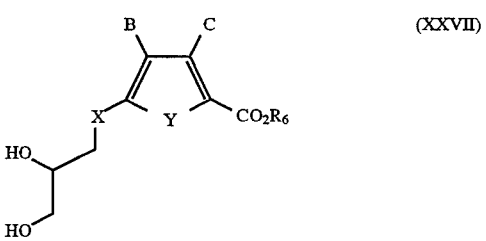

wherein B, C and Y are as defined above for formula XI; X is as defined above for formula XI, except that it is other than $CH_2$; and $R_6$ is as defined above for formula XII.

The compound of the formula XXVII is reacted with a sulfonylating agent, preferably p-toluenesulfonyl chloride or methanesulfonyl chloride, in the presence of a non-nucleophilic base, preferably triethylamine or diisopropylethylamine, to yield an intermediate mono-sulfonylated compound. This intermediate is reacted with a strong base, preferably sodium hydride, to produce a compound of formula XXVIII:

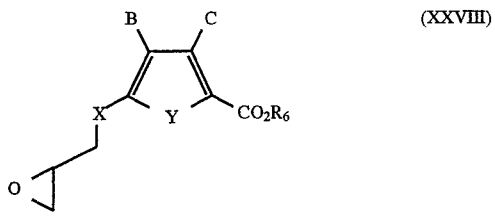

wherein B, C, X, Y and $R_6$ are as defined above for formula XXVII.

The epoxide of formula XXVIII is reacted with a nitrogen-containing nucleophile, preferably sodium azide, in the presence of a mild Lewis-acid catalyst, preferably lithium or magnesium perchlorate, to an obtain an intermediate alcohol azide. This intermediate is reduced, preferably with hydrogen gas in the presence of a metal catalyst, and subsequent protection with a suitable nitrogen-protecting group, preferably t-butoxycarbonyl, benzoxycarbonyl or benzyl, to produce a compound of the formula XVII':

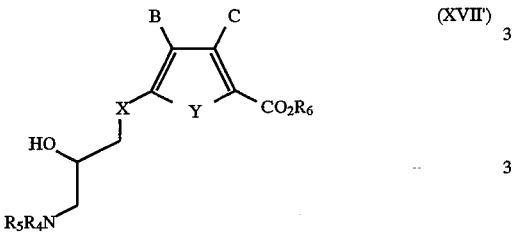

wherein B, C, X, Y and $R_6$ are as defined above for formula XXVII; and $R_4$ and $R_5$ are as defined above for formula XVI.

The compound of the formula XVII' is then reacted with an acylating or sulfonylating agent, preferably methanesulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is displaced with a suitable nucleophile, preferably a thioacid salt, more preferably potassium thioacetate, to obtain a compound of the formula XVIII':

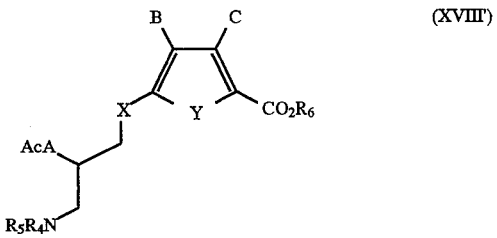

wherein A is as defined above for formula XI; B, C, X, Y and $R_6$ are as defined above for formula XXVII; $R_4$ and $R_5$ are as defined above for formula XVI; and Ac is an acyl group, preferably acetyl.

Alternatively, the compound of formula XVII' is converted to the compound of formula XVIII' in one chemical operation using triphenylphosphine, diethyl or dimethyl aza-dicarboxylate, and an acidic nucleophile, preferably thioacetic acid, in a suitable solvent.

The compound of the formula XVIII' is treated with a nucleophilic base, preferably potassium carbonate, sodium carbonate, sodium hydroxide or potassium hydroxide, in an alcoholic solvent, preferably methanol, ethanol or isopropanol, in the presence of an alkylating agent, preferably dimethyl or diethyl chloromalonate, to obtain a compound of the formula XIX':

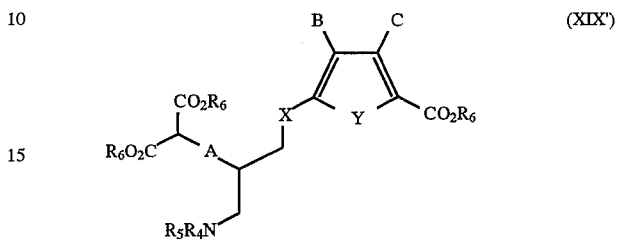

wherein A is as defined above for formula XI; B, C, X, Y and $R_6$ are as defined above for formula XXVII; and $R_4$ and $R_5$ are as defined above for formula XVI.

The compound of the formula XIX' is treated under conditions suitable to remove either or both of the $R_4$ and $R_5$ protecting groups to produce a compound of formula XX':

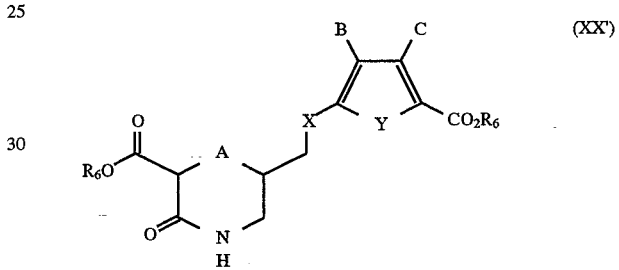

wherein A is as defined above for formula XI; and B, C, X, Y and $R_6$ are as defined above for formula XXVII. Where t-butoxycarbonyl is a protecting group, the conditions for removal of this group are preferably treatment with trifluoroacetic acid followed by neutralization to produce the compound of the formula XX'.

The compound of the formula XX' is reacted with an alkylating agent, preferably trimethyl or triethyl oxonium tetrafluoroborate, in a suitable solvent, preferably dichloromethane, to form an intermediate lactim ether. The intermediate lactim ether is reacted with guanidine in an alcoholic solvent, preferably methanol, ethanol or isopropanol, to form a compound of the formula XXI':

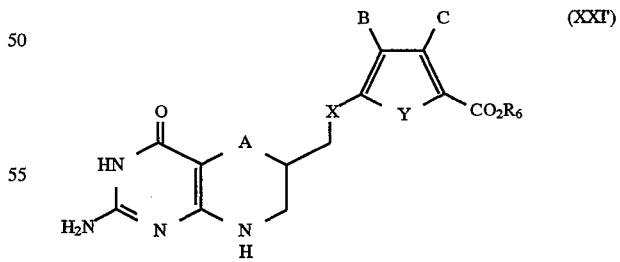

wherein A is as defined above for formula XI; and B, C, X, Y and $R_6$ are as defined above for formula XXVII.

Alternatively, the compound of the formula XX' is converted to the compound of the formula XXI' by reacting the compound of the formula XX' with a thiolating agent, preferably $P_2S_5$ or 2,4-bis(4-methoxyphenyl)-1,3-dithia-2,4-diphosphetane-2,4-disulfide, to form the thiolactam intermediate. This can then be alkylated with an alkylating agent, preferably methyl iodide or trimethyl or triethyl oxonium tetrafluoroborate, and then with guanidine in an alcoholic solvent, preferably methanol, ethanol or isopropanol, to obtain the compound of the formula XXI'.

The compound of the formula XXI' is hydrolyzed under basic conditions to form a compound of formula XXII':

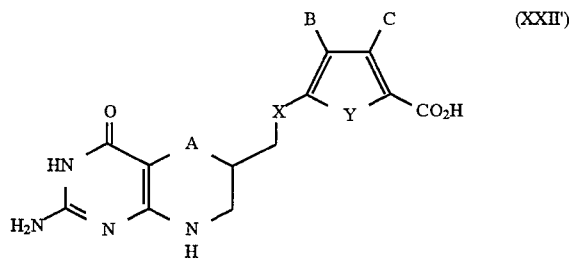

wherein A is as defined above for formula XI; and B, C, X and Y are as defined above for formula XXVII. Where $R_6$ is hydrogen in the compound of the formula XXI', then the hydrolyzation reaction is not necessary, and the compound of the formula XXI' is peptide coupled as described below.

The compound of the formula XXII' (or the compound of the formula XXI' where $R_6$ is hydrogen), which is in the free carboxylic acid form, can be peptide coupled, by means well known to those skilled in the art, with a glutamic acid diester hydrochloride to form a diester of formula XXIII':

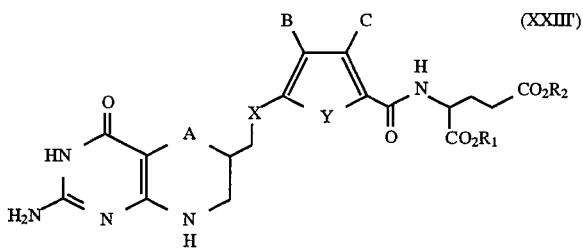

wherein A is as defined above for formula XI; B, C, X and Y are as defined above for formula XXVII; and $R_1$ and $R_2$ are each independently a moiety that forms with the attached $CO_2$ a readily hydrolyzable ester group, such as a $C_1$–$C_6$ alkyl, hydroxyalkyl, alkylaryl or arylalkyl.

Finally, if the free acid form is desired, the compound of the formula XXIII' is hydrolyzed to produce compounds of the formula XI where $R_1$ and $R_2$ are each H.

Preferred compounds of the formula XI includes (4-[2-(2-amino-4-oxo-4,6,7,8-tetrahydro-3H-pyrimido[5,4-6]-[1,4]thiazin-6-yl)-ethyl]-2,5-thienoylamino-L-glutamic acid) diethyl ester; 4-[2-(2-amino-4-oxo-4,6,7,8-tetrahydro -3H-pyrimido-[5,4-6][1,4]thiazin-6-yl)-ethyl]-2,5-thienoylamino-L-glutamic acid; 4-[3-(2-amino-4-oxo-4,6,7,8-tetrahydro-3H-pyrimido-[5,4-6][1,4]thiazin-6-yl)propyl]-2,5-thienoylamino-L-glutamic acid; 4-[2 -(2-amino-4-oxo-4,6,7,8-tetrahydro-3H-pyrimido-[5,4-6][1,4]-thiazin-6-yl)-ethyl]-3-methyl-2,5-thienoylamino-L-glutamic acid; and 4-[2-(2-amino-4-oxo-4,6,7,8-tetrahydro-3H-pyrimido -[5,4-b][1,4]thiazin-6-yl)-ethyl]-2,5-furanoylamino -L-glutamic acid.

Detailed syntheses of compounds of the invention are presented in the examples that follow.

EXAMPLE 1

2-[4-[2-(2-Amino-4-oxo-4,6,7,8-tetrahydro-3H-pyrimido[5,4-6][1,4]thiazin-6-yl-ethyl]benzoyl amino)pentanedioic acid Preparation of (1) (1,1-Dimethoxy-but-3-yn-2-ol):

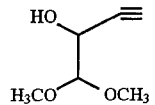

To a stirred solution of 1.037 g ( 10.55 mmol ) of trimethylsilyl acetylene in 50 ml of dry tetrahydrofuran (THF) under argon at −78° C. was added dropwise 6.6 ml of 1.6M n-butyl lithium. After 10 minutes at −78° C., a solution of 1.21 g (10.46 mmol ) of glyoxal dimethyl acetal in 5 ml of tetrahydrofuran (THF) was added dropwise. After 1 hour at −78° C., the reaction was quenched with about 1 ml of $H_2O$ and allowed to warm to room temperature, diluted with ethyl acetate and washed with saturated NaCl solution. The aqueous layer was re-extracted with ethyl acetate and combined organic layers were dried over $MgSO_4$ and concentrated under reduced pressure. To 785 mg of the resulting yellow oil dissolved in tetrahydrofuran (THF) was added 5.8 ml of 1.0M tetrabutylammonium fluoride in tetrahydrofuran (THF). After heating for 1 hour at 50° C., the volatiles were evaporated and the residue was flash chromatographed on silica eluting methylene chloride/ethyl acetate (9:1). In this manner, there was obtained 412 mg (60% overall) of the alkyne-alcohol, compound (1), as a colorless oil. IR (neat)3441 (broad), 3277, 2944, 2839, 1636, 1450, 1196, 1084 cm$^{-1}$. $^1$H NMR (CDCl$_3$) δ: 2.42 (bs, 1H), 2.49 (s,1H), 3.51 (s,3H), 3.53 (s,3H), 4.36 (bs,2H). Analysis calculated for $C_6H_{10}O_3$·0.35 $H_2O$; C, 52.81: H, 7.90 Found: C, 52.87; H, 7.86.

Preparation of (2) (4-(3-Hydroxy-4,4-dimethoxy-but-1-ynyl)benzoic acid methyl ester):

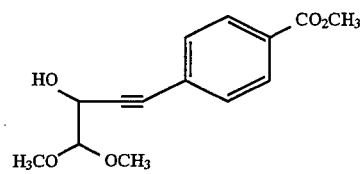

To a stirred solution of 232 mg (1.78 mmol) of the alkyne compound (1) and 467 mg (1.78 mmol) of methyl-4-Iodobenzoate in 5 ml diethylamine was added 13 mg (0.18 mmol) of bis(triphenylphosphine) palladium(II)chloride and 7 mg (0.036 mmol) of cuprous iodide. After 15 hours at room temperature, volatiles were removed under reduced pressure and the residue was flash chromatographed on silica eluting methylene chloride/ethyl acetate (12:1). In this manner, there was obtained 347 mg (74%) of the compound (2) as an orange oil. IR (neat) 3451 (broad), 2953, 2838, 1717, 1607, 1437, 1310, 1283, 1120, 1082 cm$^{-1}$. $^1$H NMR (CDCl$_3$) δ: 2.46 (bs,1H), 3.55 (s,3H), 3.56 (s,3H), 3.92 (s,3H), 4.45 (d,1H,J=5.4 Hz), 4.60 (d,1H,J=5.3 Hz), 7.52 (d,2H,J=8.3 Hz), 7.98 (d,2H,J=8.3 Hz). Analysis Calculated for $C_{14}H_{16}O_5$: C, 63.62; H, 6.10. Found: C, 63.14; H, 6.14.

Preparation of (3) (4-(3-Hydroxy-4,4-dimethoxy-butyl)-benzoic acid methyl ester):

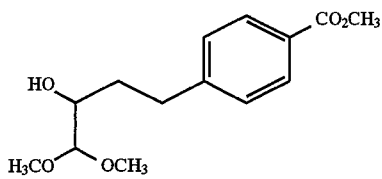

A solution containing 14.37 g (54.38 mmol) of compound (2) and 1.40 g of 5% Pd on carbon in 175 ml of ethanol was hydrogenated under 40 psi hydrogen on a Parr apparatus. After 2.5 hours, the reaction mixture was filtered and the catalyst washed with ethanol and methanol. After concentrating under reduced pressured, the residue was dissolved in methylene chloride and filtered through a short plug of silica, eluting methylene chloride, then methylene chloride/ethyl acetate (1:1) to remove the residual carbon. In this manner, there was obtained 14.34 g (98%) of the saturated alcohol, compound (3), as a yellow oil. IR (neat) 3495 (broad), 2953, 1721, 1611, 1437, 1283, 1109, 1080 cm$^{-1}$. $^1$H NMR (CDCl$_3$) δ1.72–1.93 (m,2H), 2.75–2.93 (m,2H), 3.39 (s,3H), 3.44 (s,3H), 3.58 (m, 1H), 3.90 (s,3H), 4.13 (d,1H, J=6.1 Hz), 7.29 (d,2H,J=8.1 Hz), 7.95 (d,2H,J=8.2 Hz). Analysis calculated for C$_{14}$H$_{20}$O$_5$·0.20 H$_2$O: C, 61.84; H, 7.56. Found: C, 61.83; H, 7.57.

Preparation of (4) (4- (3-Methanesulfonyloxy-4,4-dimethoxybutyl)-benzoic acid methyl ester):

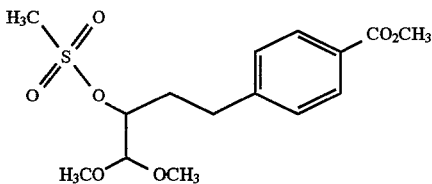

To a stirred solution of 206 mg (0.77 mmol) of saturated alcohol, compound (3), and 0.16 ml (1.15 mmol) of triethylamine in 5 ml of methylene chloride at 0° C. was added 0.07 ml (0.85 mmol) of methanesulfonyl chloride. After 20 minutes at 0° C., another 0.02 ml of methanesulfonyl chloride was added. After 30 minutes more, the reaction mixture was poured into saturated NaHCO$_3$ solution and extracted twice with methylene chloride. The combined organic layers were dried over MgSO$_4$ and the solvent was removed under reduced pressure. This material was sufficiently pure for use in the next step. An analytical sample was obtained by flash chromatography on silica eluting methylene chloride/ethyl acetate (20:1). In this manner, there was obtained the mesylate, compound (4), as a colorless oil. IR (neat), 2949, 2839, 1719, 1611, 1437, 1352, 1283, 1177, 1109, 1078 cm$^{-1}$. $^1$H NMR (CDCl$_3$) δ: 2.04 (m,2H), 2.77–2.91 (m,2H), 3.09 (s,3H), 3.41 (s,3H), 3.45 (s,3H), 3.90 (s,3H), 4.38 (d,1H,J=5.5 Hz), 4.64 (m,1H), 7.29 (d,2H,J=8.2 Hz), 7.96 (d,2H,J=8.2Hz). Analysis calculated for C$_{15}$H$_{22}$O$_7$S; C, 52.01; H, 6.40; S, 9.26. Founds C, 52.08; H, 6.44; S, 9.25.

Preparation of (5) (4-(3-Methanesulfonyloxy-4-oxobutyl) benzoic acid methyl ester):

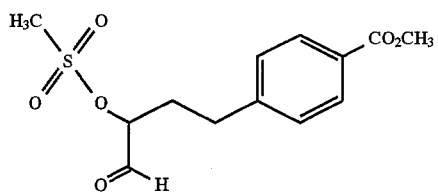

To a stirred solution of 600 mg (1.73 mmol) of dimethyl acetal (mesylate) (compound 4) in 5 ml of methyl chloride at 0° C. was added 1 ml of H$_2$O and 1 ml of trifluoroacetic acid. The reaction was warmed to room temperature, then refluxed for 24 hours. The cooled reaction mixture was diluted with ethyl acetate and washed twice sequentially with saturated NaCl solution, saturated NaHCO$_3$ solution, then again with saturated NaCl solution, dried (MgSO$_4$) and the volatiles were removed under reduced pressure. In this manner, there was obtained the mesylate, compound (5), which was used without purification. NMR (CDCl$_3$) δ: 2.20 (m,2H), 2.85 (m,2H), 3.17 (s,3H), 3.91 (s,3H), 4.95 (dd,1H, J=4.2 Hz, 8.4 Hz), 7.29 (d,2H,J=8.1 Hz), 7.99 (d,2H,J=8.2 Hz), 9.59 (s,1H).

Preparation of (6) (4-[3-(4-Methoxy-benzylsulfanyl)-4-oxobutyl]-benzoic acid methyl ester):

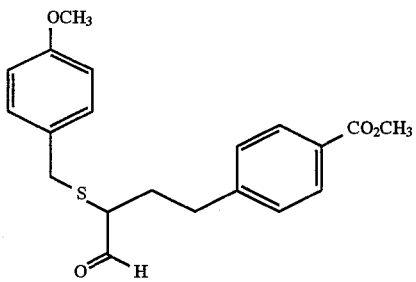

To a stirred solution of 686 mg (2.28 mmol) of the mesylate, compound (5), and 0.40 ml (2.29 mmol) of N,N-diisopropylethylamine in dimethyl formamide (DMF) was added 0.48 ml (3.44 mmol) of 4-methoxy-α-toluenethiol. After 3 hours at room temperature, the reaction mixture was poured into 0.5N HCl and extracted twice with ethyl acetate. The combined organic layers were washed twice with saturated NaCl solution, dried (MgSO$_4$), and concentrated under reduced pressure. The aldehyde obtained, compound (6), was sufficiently pure to use without further purification in the next step. IR (KBr) 2930, 1715, 1703, 1611, 1512, 1282, 1244, 1107 cm$^{-1}$. $^1$H NMR (CDCl$_3$) δ: 1.80–2.16 (m,2H), 2.75 (m,2H), 2.99 (m,1H), 3.53 (AB,2H,J=13.4 Hz), 3.81 (s,3H), 3.90 (s,3H),. 6.83 (d,2H,J=8.5 Hz), 7.12 (d,2H,J=8.2 Hz), 7.19 (d,2H,J=8.6Hz), 7.90 (d,2H,J=8.2 Hz), 9.27 (d,1H,J=4.2 Hz).

Preparation of (7) (4-[3-[1,3]Dioxolan-2-yl-3-(4-methoxybenzylsulfanyl)-propyl]-benzoic acid methyl ester):

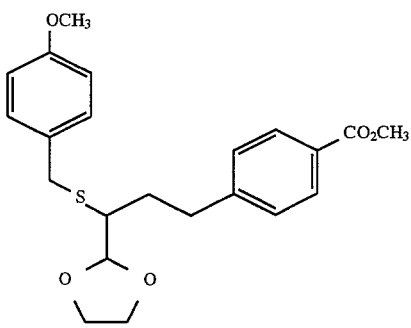

A flask containing 301 mg (0.84 mmol) of the aldehyde, compound (6), 94 μl (1.68 mmol) of ethylene glycol and 42 mg (0.17 mmol) of pyridinium p-toluenesulfonate and 30 ml of benzene was heated at reflux removing the generated water with a Dean-Stark trap. After 3 hours, the reaction mixture was poured into saturated NaCl solution and extracted twice with ethyl acetate. The combined organic layers were dried (MgSO4) and concentrated under reduced pressure. The residue was flash chromatographed on silica, eluting hexanes-ethyl acetate (5:1). In this manner, there was obtained the title compound (7) in an overall 84% yield from the mesylate dimethylacetal, compound (4). IR (neat), 2949, 2886, 1721, 1611, 1510, 1435, 1279, 1248, 1177, 1111, 1034 cm$^{-1}$. $^1$H NMR (CDCl$_3$) δ: 1.67 (m,1H), 1.99 (m,1H), 2.57 (m,2H), 2.84 (m, 1H), 3.72–4.03 (m,6H), 3.81 (s,3H), 3.90 (s,3H), 4.97 (d,1H,J =4.6 Hz), 6.83 (d,2H,J=8.6 Hz), 7.09 (d,2H,J=8.1 Hz), 7.23 (d,2H,J=8.5 Hz), 7.88 (d,2H,J=8.1 Hz). Analysis calculated for C$_{22}$H$_{26}$O$_5$S: C, 65.65; H, 6.51; S, 7.97. Found: C, 65.72; H, 6.50; S, 8.07.

Preparation of (8) (4-(3-[1,3]Dioxolan-2-yl-3-mercaptopropyl)-benzoic acid methyl ester):

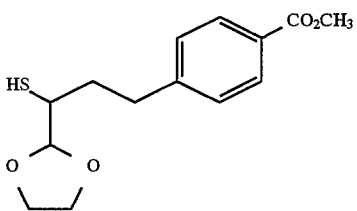

To a stirred solution of 5.70 g (14.16 mol) of compound (7) and 5.42 g (17.00 mmol) of mercuric acetate in methylene chloride, cooled to 0° C., was added, dropwise, 5 ml of trifluoroacetic acid. After 3 hours at 0° C., hydrogen sulfide saturated methanol was added and stirring was continued at 0° C. for 20 minutes. The reaction mixture was poured into saturated NaCl solution and extracted twice with methylene chloride. The combined organic layers were dried (MgSO$_4$) and concentrated at reduced pressure. To the crude residue partially suspended in methanol was added 1.07 g (28.28 mmol) of sodium borohydride in portions. After about 30 minutes, the reaction mixture was poured into ethyl acetate and 0.5N HCl and the layers separated. The metallic mercury that formed in the reaction was washed with ethyl acetate. The combined organic layers were washed with saturated NaCl solution, dried (MgSO4) and concentrated under reduced pressure. The residue was flash chromatographed on silica eluting hexanes:ethyl acetate (4:1). In this matter, there was obtained 1.99 g (50%) of the thiol, compound (8), as a light yellow oil. IR (neat), 2951, 2886, 1719, 1611, 1435, 1281, 1179, 1144, 1111 cm$^{-1}$. $^1$H NMR (CDCl$_3$) δ: 1.64 (d,1H,J=7.8 Hz), 1.74 (m, 1H), 2.15 (m, 1H), 2.80 (m,2H), 3.00 (m, 1H), 3.90 (s,3H), 3.97 (m,4H), 4.91 (d,1H,J=4.0 Hz), 7.28 (d,2H,J=8.1 Hz), 7.95 (d,2H,J= 8.1 Hz). Analysis calculated for C$_{14}$H$_{18}$O$_4$S: C, 59.55; H, 6.14. Found: C, 59.42; H, 6.41.

Preparation of (9) (4-[3-(2,4-diamino-6-oxo-1,6-dihydro-pyrimidin-5-ylsulfanyl)-3-[1,3]dioxolan-2-yl-propyl]-benzoic acid methyl ester):

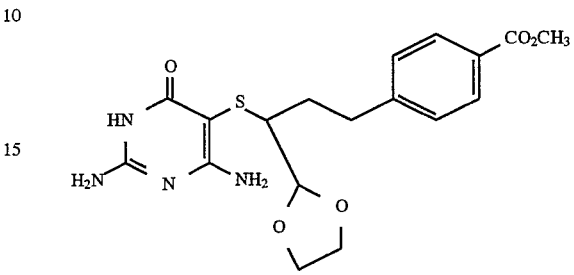

To a stirred solution of 1.91 g (6.76 mmol) of the thiol, compound (8), and 1.39 g (6.78 mmol) of 5-bromo-2,4-diamino-6-oxopyrimidine under argon in degassed N,N-dimethylformamide was added 1.18 ml (6.77 mmol) of N,N-diisopropylethylamine. The reaction mixture was heated at 90° C. for 3 hours. The cooled reaction mixture was poured into saturated NaCl solution and the precipitate which formed was collected by filtration, washed with water and air dried. The filter cake was slurried in methylene chloride. Hexanes were slowly added and the precipitate was again collected by filtration, washed with hexanes and dried. In this manner, there was obtained 1.91 g (69 %) of the desired dioxolane, compound (9), as an off-white solid (m.p. 206°–208° C. with decomposition). IR (KBr) 3439, 3341, 3154, 1701, 1636, 1591, 1470, 1447, 1287 cm$^{-1}$. $^1$H NMR (DMSO) δ: 1.64 (m, 1H), 1 84 (m, 1H), 2.58 (m, 1H), 2.79 (m, 1H), 3.19 (m, 1H), 3.82 (s,3H), 3.85 (m,4H), 4.83 (d,1H,J=4.3 Hz), 6.33 (broad s,4H), 7.33 (d,2H,J=8.1 Hz), 7.83 (d,2H,J=8.1 Hz, 10.03 (s,1H). Analysis calculated for C$_{18}$H$_{22}$N$_4$O$_5$S: C, 53.19; H, 5.46; N, 13.78; S, 7.89. Found: C, 52.98; H, 5.53; N, 13.60; S, 7.76.

Preparation of (10) (4-[2-(2-Amino-7-hydroxy-4-oxo-4, 6,7,8-tetrahydro-3H-pyrimido[5,4-6][1,4]thiazin-6-yl)-ethyl]-benzoic acid methyl ester):

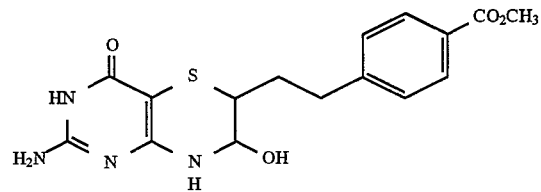

A stirred suspension of 1.20 g (2.85 mmol) of the dioxolane, compound (9), and 4 ml of 2N HCl in 20 ml of tetrahydrofuran (THF) was heated at reflux for 2.5 hours. The homogeneous solution was poured slowly into saturated NaHCO$_3$ solution and the precipitate that formed was collected. The filtrate was extracted with ethyl acetate. A precipitate (58 mg) formed between layers and was collected and combined with the first precipitate. The ethyl acetate layer was dried over MgSO$_4$ and the solvent was removed under reduced pressure. The residue (42 mg) was also combined with the original precipitate. In this manner, there was obtained 984 mg (98%) of the carbinolamine, compound (10), as an orange solid. (m.p. 213°–216° C.). IR (KBr) 3351, 3441, 1705, 1638, 1609, 1557, 1470, 1289, 1113, 1020 cm$^{-1}$. $^1$H NMR as a single pair of diastereomers (DMSO) δ: 1.39 and 1.96 (m,m, 1H), 1.70 (m, 1H), 2.56–2.89 (m,3H), 3.82 (s,3H), 4.71 and 4.84 (m,m, 1H), 5.37 and 5.40 (d,d,1H,J=6.6 Hz), 6.06 (s,2H), 7.20 (d,1H, J=4.5 Hz), 7.31 and 7.36 (d,d,2H,J=8.1 Hz), 7.86 and 7.88 (d,d,2H,J=8.0 Hz), 10.16 and 10.19 (s,s,1H). Analysis calculated for $C_{16}H_{18}N_4O_4S \cdot 1.7\ H_2O$: C 48.89; H, 5.49; N, 14.26; S, 8.16. Found: C, 48.78; H, 5.18; N, 14.00; S, 8.03.

Preparation of (11) (4-[2-(Amino-4-oxo-4,6,7,8-tetrahydro-3H-pyrimido[5,4-6][1,4]thiazin-6-yl]-benzoic acid methyl ester):

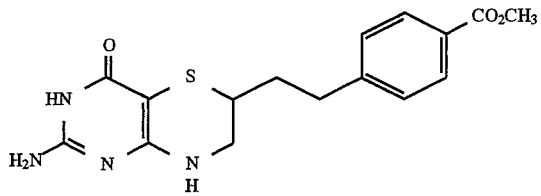

To a 0° C. suspension of 1.126 g (3.1 mmol) of carbinolamine, compound (10), in tetrahydrofuran (THF) was added 2.3 ml (18.64 mmol) of boron trifluoride etherate. When the addition was complete, 0..586 g (9.32 mmol) of sodium cyanoborohydride was added in portions over 5 minutes. After an additional 30 minutes, 5 ml of ammonia saturated methanol was added, the reaction mixture was diluted with ethyl acetate and washed with saturated NaCl solution. The organic layer was dried (MgSO$_4$) and the solvent removed under reduced pressure. The residue was flash chromatographed on silica eluting methylene chloride/methanol (9:1). In this manner, there was obtained 542 mg (50%) of the dehydrated ester, compound (11), as an orange solid: mp 245°–246° C. with decomposition. IR (KBr) 3358, 2936, 1721, 1644, 1595, 1537, 1447, 1346, 1281 cm$^{-1}$. $^1$H NMR (DMSO) δ: 1.72 (m, 1H), 1.90 (m, 1H), 2.80 (m,3H), 3.22 (m, 1H), 3.52 (m, 1H), 3.82 (s,3H), 6.00 (s,2H), 6.65 (s,1H), 7.37 (d,2H,J=8.1 Hz), 7.87 (d,2H,J=8.1 Hz), 10.05 (s,1H). Analysis calculated for $C_{16}H_{18}N_4O_3S$: C, 55.47; H, 5.24; N, 16.17; S, 9.26. Found: C, 55.31; H, 5.29; N, 16.09; S, 9.17.

Preparation of (12) (4-[2-(2-Amino-4-oxo-4,6,7,8-tetrahydro-3H-pyrimido[5,4-6][1,4]thiazin-6-yl)-ethyl]-benzoic acid):

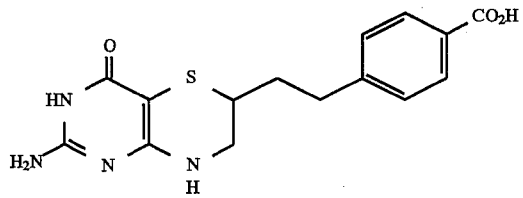

A solution of 530 mg (1.53 mmol) of the ester, compound (11), and 10 ml of 1N NaOH was stirred at room temperature for 30 minutes. The homogeneous solution was made slightly acidic (pH 4) with concentration HCl. After cooling in an ice bath, the light orange precipitate was collected by filtration and air dried. It was then suspended in ethanol and the ethanol removed under reduced pressure. In this manner, there was obtained 468 mg (91%) of the acid, compound (12) (decomposes >310° C.). IR (KBr) 3285, 3086, 2928, 1698, 1642, 1611, 1576, 1449, 1348 cm$^{-1}$. $^1$H NMR (DMSO) δ: 1.72 (m, 1H), 1.89 (m,1H), 2.78 (m,3H), 3.20 (m, 1H), 3.48 (m, 1H), 6.07 (s,2H), 6.58 (s,1H), 7.33 (d,2H,J=8.1 Hz), 7.85 (d,2H,J=8.1 Hz), 10.11 (s,1H), 12.77 (broad s,1H). Analysis calculated for $C_{15}H_{16}N_4O_3S \cdot 1.20$ $H_2O$: C, 50.89; H, 5.24; N, 15.83; S, 9.06. Found: C, 50.70; H, 4.92; N, 15.58; S, 8.87.

Preparation of (13) (2-[4-[2-(2-Amino-4-oxo-4,6,7,8-tetrahydro-3H-pyrimido[5,4-6][1,4]thiazin-6-yl)-ethyl]-benzoylamino]-pentanedioic acid diethyl ester):

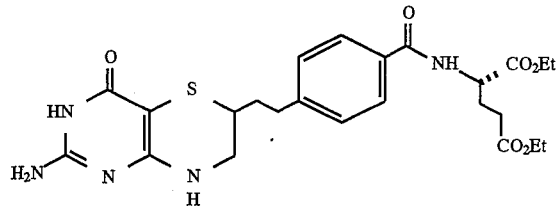

To a stirred solution of 397 mg (1.19 mmol) of the acid, compound (12), 169 mg (1.25 mmol) of 1-Hydroxybenzotriazole hydrate (HOBT), 0.22 ml (1.25 mmol) of N,N-diisopropylethylamine and 300 mg (1.25 mmol) of L-glutamic acid diethyl ester hydrochloride in 15 ml of N,N-dimethylformamide was added 240 mg (1.25 mmol) of 1-(3-dimethylaminopropyl)-3-ethyl-carbodiimide hydrochloride (EDC). After 18 hours at room temperature, the reaction mixture was poured into ice cold saturated NaCl solution and the precipitate which formed was collected, washed with H$_2$O and air dried. The precipitate was flash chromatographed on silica eluting methylene chloride/methanol (9:1). In this manner, there was obtained 357 mg (58%) of the desired product (13) as a light orange solid (m.p. 132°–136° C.). IR (KBr) 3333, 1732, 1645, 1572, 1535, 1449, 1343, 1203, 1020 cm$^{-1}$. $^1$H NMR (DMSO) δ: 1.15 (t,3H,J=7.3 Hz), 1.17 (t,3H,J=7.3 Hz), 1.72 (m, 1H), 1.88–2.10 (m,3H), 2.42 (t,2H,J=7.4 Hz), 2.79 (m,3H), 3.22 (m, 1H), 3.50 (m, 1H), 4.02 (q,2H,J=7.3, 14.5 Hz), 4.09 (g,2H,J=7.2, 14.3 Hz), 4.41 (m, 1H), 6.21 (s,2H), 6.74 (s,1H), 7.32 (d,2H,J=8.0 Hz), 7.80 (d,2H,J=8.0 Hz), 8.64 (d,1H,J=7.41 Hz), 10.24 (s,1H). Analysis calculated for $C_{24}H_{31}N_5O_6S$: C, 55.69; H, 6.04; N, 13.53; S, 6.19. Found: C, 55.41; H, 6.11; N, 13.48; S, 6.12.

Preparation of (14) (2-[4-[2-(2-Amino-4-oxo-4,6,7,8-tetrahydro-3H-pyrimido[5,4-6][1,4]thiazin-6-yl)-ethyl]benzoyl amino)pentanedioic acid):

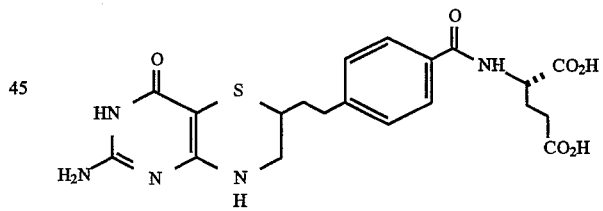

A mixture of 320 mg (0.618 mmol) of flutamate, compound (13), and 6 ml of 1N NaOH was stirred at room temperature for 3 hours, neutralized with concentrated HCl, then made slightly acidic with 2N HCl. After cooling, the light yellow precipitate was collected and air dried. The filter cake was taken up in ethanol/acetonitrile and any residual H$_2$O was azeotroped off. In this manner, there was obtained 220 mg (77%) of the diacid, compound (14) (m.p. 188°–190° C.). IR (KBr) 3348 (broad), 2930, 1717, 1642, 1539, 1505, 1348 cm$^{-1}$. $^1$H NMR (DMSO) δ: 1.71 (m, 1H), 1.92 (m,2H), 2.08 (m, 1H), 2.34 (t,2H,J=7.4 Hz), 2.79 (m,3H), 3.20 (m, 1H), 3.55 (m, 1H), 4.38 (m, 1H), 6.07 (s,2H), 6.68 (s,1H), 7.31 (d,2H,J=8.1 Hz), 7.80 (d,2H,J=8.2 Hz), 8.53 (d,1H,J=7.7 Hz), 10.11 (s,1H), 12.40 (broad s,2H). Analysis calculated for $C_{20}H_{23}N_5O_6S \cdot 1.5\ H_2O$: C, 49.17; H, 5.36; N, 14.34; S, 6.56. Found: C, 48.77; H, 4.97, N, 14.07; S, 6.54.

Biological and Biochemical Evaluation
In Vitro Testing:

Cellular growth in the presence of the compounds according to the present invention was assessed using the L1210 murine leukemia (ATCC CCL 219) cell line. The cell line was maintained in RPMI 1640 medium containing 5% heat-inactivated fetal bovine serum without antibiotics.

$IC_{50}$ values were determined in 160 microliter microcultures containing 1500 (L1210) cells established in 96-well plates in growth medium supplemented with 50 IU/ml penicillin and 50 mcg/ml streptomycin. Growth was measured over 3 days of continuous exposure to varying concentrations of the test compound added 4 hours after initial cell plating by the MTT-tetrazolium reduction assay of Mosmann, *Immunol. Math.* 65 (1983), 55–63, modified according to Alley et al., *Cancer Res.* 48 (1988), 589–601. Water insoluble derivatives were dissolved in DMSO and diluted to a final concentration of 0.5% solvent in cell cultures. Determination of Inhibition Constants for Gar Transformylase:

GAR transformylase inhibition constant was measured by the method of Cleland, *Biochem. Biophys. Acta* 67 (1963), 173–187. Assays were done at 22° C. and initiated by addition of enzyme using the spectrophotometric assay of Young et al., *Biochemistry* 23 (1984), 3979–3986, and monitoring the reaction at 295 nm. The GAR transformylase domain of the human enzyme was used. The variable substrate was 10-formyl-5-8-dideazafolate at concentrations of 0.83 µM, 1.25 µM, 2.5 µM and 5 µM, while the other substrate, GAR (glycinamide ribonucleotide), was held constant at 20 µM. The assay mix contained 20 mM Hepes pH 7.5, 20 µM GAR, and variable amounts of 10-formyl-5,8-dideazafolate and the test compound (14). For the test compound, five concentrations were used ranging from 0 to approximately 3 $K_i$. The data were plotted as the velocity of the reaction versus the reciprocal of the 10-formyl-5,8-dideazafolate concentration. The inhibition constant was measured from a replot of the slopes of these lines obtained for each concentration of inhibitor versus the inhibitor concentration.

TABLE 1

Data for Compound 14
GARFT Inhibition and Cell Culture Data

| Compound | GARFT $K_i$ (µM) | $IC_{50}$ Cell Culture L1210 (µM) |
|---|---|---|
| 14 | 0.035 | 0.05 |

EXAMPLE 2

4-[2-(2-Amino-4-oxo-4,6,7,8-tetrahydro-3H-pyrimido[5,4-6]-[1,4]thiazin-6-yl)-ethyl]-2,5-thienoylamino-L-glutamic acid
Synthesis Preparation (22) (Methyl-5-bromo-2-thiophene carboxlate):

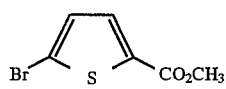

Compound (22) (CAS Reg. No. [62224-19-5]) was prepared as described at S. Gronowitz, *Ark. Kemi* 8, 1955, 87, and S. O. Lawesson, *Ark. Kemi* 11, 1957, 337.

Preparation of (23) (5-Ethynyl-2-carbomethoxy thiophene):

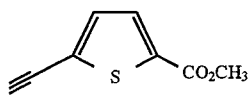

To a stirred solution of 5 g (22.7 mmol) of the bromide (23), 160 mg (0.23 mmol) of tris-triphenylphosphine palladium(II) chloride and 65 mg (0.34 mmol) of cuprous iodide in 75 ml of diethylamine was added 4.8 ml (34 mmol) of trimethylsilyl acetylene. The resultant solution was stirred at 25° C. After 18 hours, the solvent was removed under reduced pressure, and the crude residue was dissolved in 300 ml $Et_2O$ (diethyl ether) and extracted with 100 ml of 1N HCl and 100 ml of saturated bicarbonate, solution. The organic layer was dried ($Na_2SO_4$) and the solvent was removed under reduced pressure. The crude residue was flash chromatographed on silica gel with 5% $Et_2O$/hexanes to give 4.4 g (81% yield) of the silyl-protected product as a yellow solid. This material was used directly in the next step.

To a solution of 4.4 g (18.5 mmol) of the above silyl-protected acetylene in 50 ml of dimethylformamide (DMF) was added 3.3 g (35.2 mmol) of potassium fluoride monohydrate. After 15 minutes at 25° C. the mixture was poured into 500 ml of $Et_2O$ and extracted four times with 100 ml of water (4×100 ml $H_2O$). The organic solution was dried ($Na_2SO_4$), and the solvent was removed under reduced pressure. The crude residue was flash chromatographed on silica gel with 10% $Et_2O$/hexanes to give 2.65 g (86% yield) of the desired product (23) as an orange solid. NMR ($CDCl_3$) δ: 3.45 (s, 1H), 3.88 (s, 3H), 7.22 (d, 1H, J=3.5 Hz), 7.65 (d, 1H, J=3.5Hz). Anal. Calcd. for $C_8H_6SO_2$: C, 57.81; H, 3.64; S, 19.29. Founds C, 57.91; H, 3.71; S, 19.18.

An alternate method for the removal of the silyl group was also used as follows. To a stirred suspension of 3.7 g (0.02 mol) of anhydrous $K_2CO_3$ in 700 ml of methanol was added 59.7 g of the silyl-acetylene prepared above as a solid. The suspension was stirred for 2 hours at 35° C. and then the methanol was evaporated The residue was added to 50 ml of water and this was extracted with 3×150 ml $Et_2O$, and the combined organic fractions were dried ($Na_2SO_4$) and evaporated. The crude residue was chromatographed on flash silica gel using 7% $Et_2O$/hexanes to give the desired product (23) in 98% yield (38.72 g).

Preparation of (24) (N-(t-Butoxycarbonyl)-glycinal):

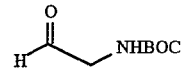

To a stirred solution of 2 g (12.4 mmol) of N-(t-butoxy-carbonyl)-2-hydroxy-ethylamine (obtained from Sigma Chemicals) in 80 ml of $CH_2Cl_2$ at −78° C. was added 1.3 ml (18.6 mmol) of dimethyl sulfoxide (DMSO) and 1.2 ml (13.7 mmol) of oxalyl chloride. After 5 minutes, 5.4 ml (38.4 mmol) of triethylamine was added and the solution was allowed to warm to 25° C. The mixture was poured into 200 ml of $Et_2O$ and extracted with 100 ml of water, 100 ml of 0.5N HCl, and 100 ml of saturated bicarbonate solution. The organic fraction was dried ($Na_2SO_4$), and the solvent was removed under reduced pressure. The crude aldehyde was dissolved in 100 ml benzene, and the solvent was again removed under reduced pressure. This crude material, which was found to be unstable, was used immediately in the next step.

Preparation of (25) (4-N-(t-butoxycarbonyl)-3-hydroxy-1-(2-carbomethoxy-5-thiophene)-butyne):

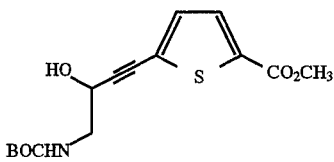

To a solution of 1.7 g (10.2 mmol) of acetylene (23) in 10 ml of dry tetrahydrofuran (THF) at −78° C. was added 14.3 ml (14.0 mmol) of a 1M solution of lithium bis-trimethylsilyl amide in THF. After 10 minutes, the crude aldehyde (24) from above was added dropwise in 5 ml of dry THF. The solution was stirred at −78° C. for 10 minutes and allowed to warm to 0° C. over a twenty-minute period. To this was added 5 ml of a saturated aqueous solution of ammonium chloride. The mixture was poured into 200 ml of $Et_2O$ and washed with 100 ml of $H_2O$ and then 50 ml of saturated NaCl solution. The organic layer was dried ($Na_2SO_4$) and the solvent was removed under reduced pressure. The crude residue was flash chromatographed on silica gel with 10–40% EtOAc/hexanes to give 0.96 g (29%) of the desired alcohol (25) as a slightly yellow oil. NMR ($CDCl_3$) δ: 1.46 (s, 9H), 3.38 and 3.58 (AB, 2H, J=3, 7 Hz), 3.88 (s, 3H),, 4.71 (dt, 1H, J=2.9, 5.2 Hz), 5.05 (brs, 1H), 7.15 (d, 1H, J=3.9 Hz), 7.64 (d, 1H, J=3.9 Hz). IR (neat): 2978.3, 1729.5, 1685, 1523, 1452, 1368, 1286, 1167, 1098, 959, 822, 750.4 $cm^{-1}$. High Resolution Mass Spec , Calcd for $C_{15}H_{19}NO_5S$: $M^+Cs^+$, 458.0038. Found: 458.0051.

Preparation of (26) (Methyl-5- [(4-N-(t-butoxycarbonyl)-amino -3-hydroxy)-butyl]-thienyl-2-carboxylate):

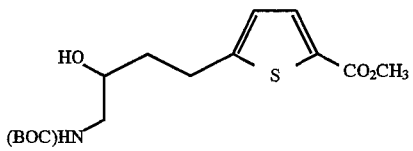

To a stirred solution of 940 mg (2.89 mmol) of the above acetylene (25) in 50 ml of ethylacetate (EtOAc) was added 320 mg of 5% Pd/C. The mixture was placed under 40 psi of $H_2$ gas and stirred at 25° C. for 17 hours. The mixture was filtered through Celite (diatomaceous earth) and the solvent was removed under reduced pressure. The crude residue was flash chromatographed on silica gel with 20% EtOAc/ $CH_2Cl_2$ to give 800 mg (84% yield) of the desired alcohol as a yellow oil. NMR ($CDCl_3$) δ: 1.44 (s, 9H), 1.81 (m, 2H), 2.28 (brs, 1H), 2.99 (m, 2H), 3.10 and 3.29 (AB, 2H, J=3, 6.9 Hz), 3.74 (m, 1H), 3.86 (s, 3H), 4.89 (brs, 1H), 6.82 (d, 1H, J=3.7 Hz), 7.63 (d, 1H, J=3.7 Hz). Anal. Calcd. for $C_{15}H_{23}NO_5S$: C, 54.69; H, 7.04; N, 4.25; S, 9.73. Found: C, 54.79; H, 7.02; N, 4.29; S, 9.63.

An alternate method for the preparation of alcohol (26) uses bis-t-butoxycarbonyl allylamine (34) as follows.

Preparation of (34) (Bis-t-butoxycarbonyl allylamine):

To a solution of 57.10 g (1.0 mol) of allylamine and 1.2 g (0.01 mol) of dimethylaminopyridine (DMAP) in 500 ml of acetonitrile was added a solution of 220 g (1 mol) of (t-BOC)$_2$O in 100 ml of acetonitrile, and the resultant mixture was stirred for 6 hours. The reaction mixture was diluted with toluene (100 ml) and the solvents were evaporated under reduced pressure at 60° C. The resultant oil was re-dissolved in acetonitrile (400 ml) and another 1.2 g (0.01 mol) of DMAP was added, and to this a solution of 220 g (1 mol) of (t-BOC)$_2$O in 100 ml of acetonitrile was slowly added. The reaction mixture was stirred for 12 hours at 60° C. the solvent was evaporated under reduced pressure at 60° C., and dilute $NaHCO_3$ (100 ml) was added. This was extracted with 3×150 ml $CH_2Cl_2$, and the combined organic layers were washed with brine, dried ($Na_2SO_4$) and evaporated. The crude residue was purified by chromatography on flash silica gel eluting with a gradient of 5–20% EtOAc/hexanes to give 156.9 g (63% yield) of the desired product (34) as a clear crystalline solid (m.p. 43°–44° C). $^1H$ NMR ($CDCl_3$) δ (ppm): 1.5 (s, 18H), 4.18 (dd, 2H, J=15 Hz, J=1 Hz), 5.14 (ddd, 2H, J=15 Hz, J=10 Hz, J=1 Hz), 5.85 (ddt, 2H, J=10 Hz, J=5 Hz, J=1 Hz). IR (KBr): 2978, 2935, 2860, 1724, 1689, 1342, 1130 cm . Anal. Calcd. for $C_{13}H_{23}NO_4$: C, 60.68; H, 9.01; N, 5.44. Found: C, 60.78; H, 9.04; N, 5.50.

Preparation of (35) (1-(bis-t-Butoxycarbonyl amino)-2-ethanal):

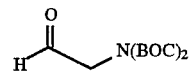

A solution of 0.60 g (2.34 mmol) of bis-t-butoxycarbonyl allylamine (34) in 20 ml of $CH_2Cl_2$ was ozonized (40 volts, 500 amperes, 1.0 l/min. $O_2$@3 psi) at −78° C. until a blue color persisted, 10 ml of dimethyl sulfide was added, and this mixture was stirred for 14 hours at 25° C. The mixture was added to dilute brine and extracted with $CH_2Cl_2$ (3×50 ml), and the organic fractions were dried ($Na_2SO_4$) and evaporated. Chromatography using flash silica gel yielded 603 mg (99% yield) of the desired product (35) as a clear crystalline solid (m.p. 37°–39° C.). $^1H$ NMR ($CDCl_3$) δ (ppm): 1.50 (s, 18H), 4.38 (s, 2H), 9.55 (s, 1H). IR (KBr): 2984, 2935, 2724, 1792, 1734, 1699, 1362, 1153 $cm^{-1}$. Anal. Calcd. for $C_{12}H_{21}NO_5$: C, 55.58; H, 8.16; N, 5.40. Found: C, 55.20; H, 8.19; N, 5.19.

Preparation of (26) (Methyl-5-[(4-N-(t-butoxycarbonyl)-amino -3-hydroxy)-butyl]-thienyl-2-carboxylate):

To a solution of 9.64 g (59 mmol) of 5-ethynyl-2-carbomethoxy thiophene (23) in THF (250 ml) at −78° C. was added 65.6 ml (60 mmol, 0.9M) of lithium hexamethyl disilazide (LiHMDS), and the mixture was stirred for 2 hours at −78° C. A solution of 15.6 g (60 mmol) of 1-(bis-t-butoxyxcarbonylamino)-2-ethanal (35) in THF (40 ml) was cannulated into the reaction mixture, and the mixture was stirred for 8 hours at −78° C. A solution of 3.4 ml (60 mmol) acetic acid in methanol (10 ml) was added as a quench, the mixture was stirred for 10 minutes warming to 0° C., and water (60 ml) was added. This was extracted with EtOAc (3×100 ml), and the organic extracts were washed with dilute $NaHCO_3$ and dried ($Na_2SO_4$). The solvent was removed by reduced pressure to approximately 50 ml. To the resulting residue was added EtOAc (125 ml), and this solution was added to a Parr bottle containing 7.38 g (30 wt. % of acetylene starting material) of 5% Pd on carbon and hydrogenated at 55 psi of $H_2$ for 24 hours. The crude hydrogenation material was filtered through Celite, and the filter cake was washed with methanol (100 ml) and StOAc (100 ml). The solvent was evaporated under reduced pressure, the crude residue was filtered through silica eluting with 50% EtOAc in hexanes, and the solvent was evaporated. The residue was solvated in 20 ml of methanol (MeOH) azeotroped with benzene (50 ml), and re-dissolved in dry MeOH (20 ml). This mixture was added to a freshly prepared solution of 60 ml (2M) of sodium methoxide in methanol. The reaction mixture was stirred for 45 minutes, dilute HCl (0.1M, 50 ml) was added, and this mixture was extracted with EtOAc (3×75 ml). The organic fractions were combined and washed with pH 7 buffer (1M), dried ($Na_2SO_4$) and evaporated. The crude residue was chromatographed on flash silica eluting with 40% EtOAc/hexanes to give 9.32 g (48% yield) of the desired product (26).

Preparation of (27) (Methyl-5-[(4-N-(t-butoxycarbonyl) -amino-3-acetylthio)-butyl]-2-thiophenecarboxylate):

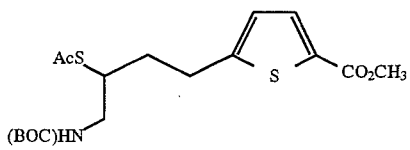

To a stirred solution of 9.26 g (28.1 mmol) of the alcohol (26) in 100 ml of THF at 0° C. was added 5.9 ml (42 mmol) of triethylamine (TEA) and 2.4 mi. (31 mmol) of methanesulfonyl chloride. After 20 minutes, 100 ml of DMF and 12.8 g (110 mmol) of potassium thioacetate were added, and the resultant solution was allowed to warm to 25° C. After three days, the mixture was poured into 500 ml of water and extracted with 800 ml of $Et_2O$. The organic layer was washed with 200 ml of water, 200 ml of 1N HCl, 200 ml of saturated bicarbonate solution, and 100 ml of saturated NaCl solution. The organic layer was dried ($MgSO_4$) and the solvent was removed under reduced pressure. The crude residue was flash chromatographed on silica gel with 25% EtOAc/hexanes to give 10.3 g (95% yield) of the desired thioacetate (27) as a yellow oil. NMR ($CDCl_3$) δ: 1.44 (s, 9H), 1.91 and 2.04 (ABm, 2H), 2.37 (s, 3H), 2.96 (m, 2H), 3.36 (m, 2H), 3.61 (m, 1H), 3.86 (s, 3H), 4.74 (brs, 1H), 6.79 (d, 1H, J=3.6Hz), 7.62 (d, 1H, J=3.6Hz). IR (neat): 3366, 2976.4, 1713, 1520, 1462.1, 1366, 1290.5, 1267.3, 1169, 1098, 752, 631 $cm^{-1}$. High Resolution Mass Spec., Calcd. for $C_{17}H_{25}NO_5S_2$: $M^+C^+$, 520.0229. Found: 520.0240.

Preparation of (28) (Methyl-5-[(4-N-(t-butoxycarbonyl)- amino-3-(dimethylmalonyl)thio)-butyl]-2- thiophenecarboxylate):

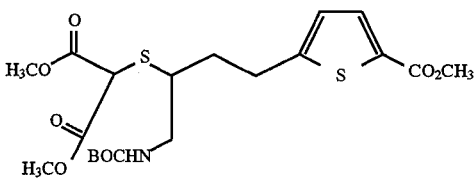

To a stirred solution of 10.2 g (26 mmmol) of the above thioacetate (27) in 200 ml of dry methanol at 0° C. was added 7.2 g (52 mmol) of $K_2CO_3$ and 3.7 ml (29 mmol) of dimethyl chloromalonate. After three hours, the mixture was poured into 500 ml of water and extracted with $Et_2O$ (3×500 ml). The combined organic layers were washed with 500 ml of water and then with 200 ml of saturated NaCl solution, and dried ($MgSO_4$). The solvent was removed under reduced pressure and the crude residue was flash chromatographed on silica gel with 30% EtOAc/hexanes to give 11.46 g (93% yield) of the desired thioether (28) as a slightly yellow oil. NMR ($CDCl_3$) δ: 1.44 (s, 9H), 1.85 and 2.00 (ABm, 2H), 3.03 (m, 3H), 3.30 (m, 2H), 3.80 (s, 6H), 3.86 (s, 3H), 5.10 (brs, 1H), 6.82 (d, 1H, J=3.8 Hz), 7.63 (d, 1H, J=3.8 Hz). IR (neat): 3442, 2974, 2955, 1734, 1713, 1512, 1460, 1435, 1366, 1291, 1267, 1167, 1098, 1022, 752 $cm^{-1}$. High Resolution Mass Spec., Calcd. for $c_{20}H_{29}NO_8S_2$: $M^+Cs^+$, 608.0389. Found: 608.0370.

Preparation of (29) (6-[(5-Carbomethoxythien-2-yl)- ethyl]-2-carbomethoxy-3-oxo-3,4,5,6-tetrahydro-[1,4]- thiazine):

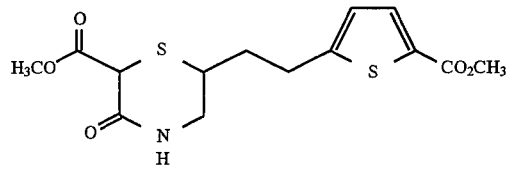

To a stirred solution of 470 mg (0.99 mmol) of the above thioether (28) in 12 ml of $CH_2Cl_2$ at 0° C. was added 4 ml of trifluoroacetic acid (TFA). After 1.5 hours, the mixture was poured into 50 ml of saturated bicarbonate solution and extracted with $CH_2Cl_2$ (4×100 ml). The solvent was removed under reduced pressure and the crude residue was dissolved in 10 ml of methanol. After stirring at 25° C. for 1.5 hours, the solvent was removed under reduced pressure and the crude residue was flash chromatographed on silica gel with 40% EtOAc/$CH_2Cl_2$ to give 298 mg (88% yield) of the desired lactam (29) as a colorless oil. NMR ($CDCl_3$) δ: 1.94 (m, 2H), 3.01 (m, 2H), 3.4–3.7 (m, 4H), 3.80 and 3.82 (s, 3H), 3.87 (s, 3H), 6.25 (brs, 1H,), 6.83 (d, 1H, J=3.7 Hz), 7.64 (d, 1H,J=3.7 Hz). IR (KBr): 2951, 1732, 1669, 1462, 1294, 1267, 1194, 1157, 1098, 1005, 752 $cm^{-1}$. Anal. Calcd. for $C_{14}H_{17}NO_5S_2$: C, 48.96; H, 4.99; N, 4.08; S, 18.67. Found: C, 49.06; H, 4.93; N, 4.09; S, 18.60.

Preparation of (30) (Methyl-[2-(2-amino-4-oxo-4,6,7,8- tetrahydro-3H-pyrimido[5,4-6][1,4]thiazin-6-yl)-ethyl]-2,5- thienoate):

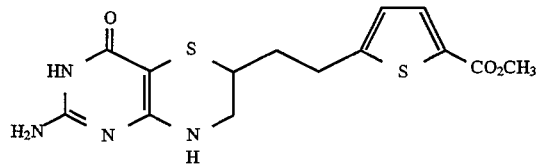

To a stirred solution of 1.9 g (5.5 mmol) of the above lactam (29) in 150 ml of dry $CH_2Cl_2$ was added, all at once, 1.06 g (7.2 mmol) of trimethyloxonium tetrafluoroborate. The solution was stirred for 6 hours at 25° C. The resulting mixture was poured into 50 ml of 10% aqueous $K_2CO_3$ and extracted with $CH_2Cl_2$ (3×200 ml). The combined organic layers were dried ($MgSO_4$) and the solvent was removed under reduced pressure. The resulting material was used directly in the next step.

In a separate flask was placed 1.58 g (16.6 mmol) of dry guanidine hydrochloride. To this was added 600 ml of dry methanol. Dry argon was bubbled through the solution for 10 minutes, after which was added 926 mg (17.1 mmol) of dry sodium methoxide. To the resultant mixture was added via a cannula the crude lactim ether prepared above in 20 ml MeOH. The solution was refluxed under an argon atmosphere for 20 hours. The pH was adjusted to 4 with 1N HCl, and the solvent was removed under reduced pressure. The crude residue was dissolved in 500 ml of $CHCl_3$ and washed with 2×100 ml of water. The organic layer was dried ($MgSO_4$), and the solvent was removed under reduced pressure. The crude residue was flash chromatographed on silica gel with 5–10% MeOH/$CH_2Cl_2$ to give 413 mg of an off-white solid. This material was then dissolved in 25 ml of hot MeOH and slowly cooled to 4° C. over an 18-hour period. The solid was collected by filtration to give 180 mg (9% yield) of the desired pyrimidinone (30) as a slightly yellow solid. NMR (d$_6$-DMSO) δ: 1.72 (m, 1H), 1.88 (m, 1H), 2.8–3.22 (m, 4H), 3.50 (dt, 1H, J=2, 8 Hz), 5.99 (brs, 2H), 6.64 (brs, 1H), 6.98 (d, 1H, J=3.8 Hz), 7.62 (d, 1H, J=3.8 Hz), 10.02 (brs, 1H). High Resolution Mass Spec., Calcd. for C$_{14}$H$_{16}$N$_4$O$_3$S$_2$: M$^+$Na$^+$, 375.0562. Found: 375.0550.

An alternate procedure for the preparation of pyrimidinone (30) was also used as follows. To a stirred solution of 500 mg (1.46 mmol) of the lactam (29) in 20 ml of dry THF was added 648 mg (1.60 mmol) of Lawesson's reagent (2,4-bis(4-methoxyphenyl) -1,3-dithia-2,4-diphosphetane-2, 4-disulfide). After the mixture was stirred at 25° C. for 20 hours, it was poured into 50 ml of saturated bicarbonate solution and extracted with 2×200 ml of EtOAc. The combined organic layers were washed with 50 ml of saturated NaCl solution and dried (MgSO$_4$), and the solvent was removed under reduced pressure.. The crude thiolactam was flash chromatographed on silica gel with 8% EtOAc/CH$_2$Cl$_2$ to give 525 mg of the corresponding thiolactam (31):

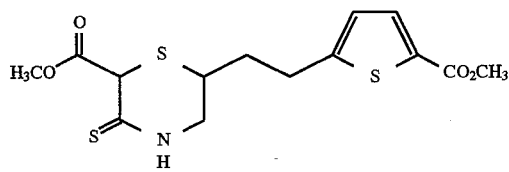

This material was used immediately in the next step.

To the 525 mg of the thiolactam (31) in a mixture of 10 ml of dry THF and 10 ml of dry methanol was added 1.6 ml of 1N NaOH. To this was added 0.1 ml (1.6 mmol) of methyl iodide to produce a methylated thiolactam, which was used as described below without purification. In a separate flask was placed 1.39 g (14.6 mmol) of dry guanidine hydrochloride. To this was added 300 ml of dry methanol. Dry argon was bubbled through the solution for 10 minutes, after which was added 796 mg (14.7 mmol) of dry sodium methoxide. To the resultant mixture was added via a cannula the crude methylated thiolactam prepared above. The solution was refluxed under an argon atmosphere for 48 hours. The pH was adjusted to 4 with 1N HCl and the solvent was removed under reduced pressure. The crude residue was dissolved in 500 ml of CHCl$_3$ and washed with 2×100 ml of water. The organic layer was dried (MgSO$_4$) and the solvent was removed under reduced pressure. The crude residue was flash chromatographed on silica gel with 5–10% MeOH/ CH$_2$Cl$_2$. The material was then dissolved in 20 ml of hot MeOH and slowly cooled to 4° C. over an 18-hour period. The solid was collected by filtration to give 131 mg (9% yield) of the desired pyrimidinone (30).

Preparation of (32) ([2-(2-Amino-4-oxo-4,6,7,8-tetrahydro -3H-pyrimido[5,4-6][1,4]thiazin-6-yl)-ethyl]-2, 5-thienoic acid):

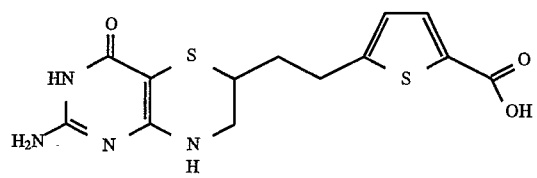

To 180 mg (0.51 mmol) of the pyrimidinone (30) was added 5 ml of 1N NaOH in water. The resulting solution was stirred at 25° C. for 20 hours. After cooling 0° C., the pH was adjusted to 2 with 1N HCl. The brown solid was filtered off and washed with water and dried under vacuum to give 111 mg (64% yield) of the desired acid (32) as a slightly brown solid. NMR (d$_6$-DMSO) δ: 1.72 (m, 1H), 1.92 (m, 1H), 2.78–3.68 (m), 6.07 (brs, 2H), 6.68 (brs, 1H), 6.92 (d, 1H, J=3.7Hz), 7.52 (d, 1H, J=3.7Hz), 10.12 (brs, 1H), 12.89 (brs, 1H). High Resolution Mass Spec., Calcd. for C$_{13}$H$_{14}$N$_4$O$_3$S$_2$: M$^+$, 338.0507. Founds 338.0517.

Preparation of (33) (4-[2-(2-Amino-4-oxo-4,6,7,8-tetrahydro -3H-pyrimido[5,4-6][1,4]thiazin-6-yl)-ethyl]-2, 5-thienoylamino -L-glutamic acid diethyl ester):

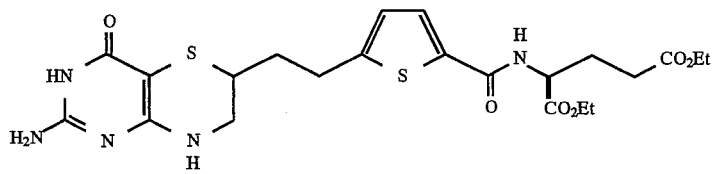

To a stirred solution of 110 mg (0.33 mmol) of the above acid (32) in 5 ml of dry DMF was added 48 mg (0.36 mmol) of 1-hydroxybenzotriazole hydrate, 62 µl (0.36 mmol) of diisopropylethylamine, 86 mg (0.36 mmol) of glutamic acid diethyl ester hydrochloride, and 106 mg (0.36 mmol) of 1-(3-dimethylamino -propyl)-3-ethylcarbodiimide methiodide. The resultant solution was stirred under an argon atmosphere at 25° C. for 20 hours and then poured into 50 ml of water. The water was extracted with 2×150 ml of EtOAc. The combined organic layers were back-extracted with 3×50 ml of water and then 10 ml of saturated NaCl solution, and dried (MgSO$_4$). The solvent was removed under reduced pressure, and the crude residue was flash chromatographed on silica gel with 0–10% MeOH/CH$_2$Cl$_2$ to give 120 mg (71% yield) of the desired amide (33) as a slightly yellow amorphous solid. NMR (d$_6$-Acetone) δ: 1.20 (m, 6H), 2.2 (m, 1H), 2.46 (t, 1H, J=7.6Hz), 2.78 (s, 1H), 2.82 (s, 1H), 2.92–3.1 (m, 2H), 3.41 (m, 1H), 3.72 (dr, 1H, J=3.0, 12.7 Hz), 4.02–4.2 (m, 4H), 4.58 (m, 1H), 5.90 (brs, 1H), 6.05 (brs, 1H), 6.90 (d, 1H, J=3.8 Hz), 7.58 (d, 1H, J=3.8 Hz), 7.78 (d, 1H, J=8 Hz). High Resolution Mass Spec., Calcd. for C$_{22}$H$_{29}$N$_5$O$_6$S$_2$: M$^+$H$^+$, 524.1638. Found: 524.1650.

Preparation of (21) (4-[2-(2-Amino-4-oxo-4,6,7,8-tetrahydro -3H-pyrimido[5,4-6][1,4]thiazin-6-yl)-ethyl]-2,5-thienoylamino -L-glutamic acid):

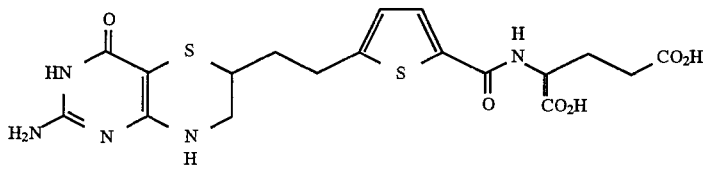

To 115 mg (0.22 mmol) of the above diethyl ester (33) was added 3 ml of 1N NaOH solution in water. The resulting mixture was stirred at 25° C. for 14 hours. After cooling to 0° C., the pH was adjusted to 3.5 with aqueous HCl. The solid was filtered, washed with water and dried under vacuum to give 82 mg (80% yield) of the desired acid (21) as an off-white solid. NMR ($d_6$-DMSO) δ: 1.62–2.02 (m, 4H), 2.27 (m, 2H), 2.78–3.00 (m, 3H), 4.27 (dd, 1H, J=6, 6.8 Hz), 6.00 (brs, 2H), 6.63 (brs, 1H), 6.88 (d, 1H, J=3.7 Hz), 7.63 (d, 1H, J=3.7 Hz), 8.37 (d, 1H, J=7.4 Hz), 10.05 (brs, 1H), 12.85 (brs, 2H). IR (KBr): 3371, 1700, 1643, 1543, 1345 cm$^{-1}$. High Resolution Mass Spec , Calcd for $C_{18}H_{21}N_5O_6S_2$: M$^+$H$^+$, 468.1012. Found: 468.1025. Anal. Calcd. for $C_{18}H_{21}N_5O_6S_2 \cdot 1.5 H_2O$: C, 43.71; H, 4.89; N, 14.16; S, 12.97. Found: C, 43.50; H, 4.67; N, 14.07; S, 12.72.

Biological and Biochemical Evaluation

Determination of Inhibition Constants for GAR Transformylase:

The GAR-transformylase (GARFT) assay method of Young et al., Biochemistry23 (1984), 3979–3986, was modified and used as described below. Reactions mixtures contained the catalytic domain of the human GARFT, 0–250 nM of test compound, 20 μM glycinamide ribonucleotide (GAR), 10 or 20 μM N$^{10}$-formyl-5,8-dideazafolate (FDDF), 50 mM HEPES-KOH, pH 7.5, and 50 mM KCl. The reaction was initiated with the addition of enzyme to a final concentration of 11 nM, followed by monitoring of the increase in absorbance at 294 nm at 20° C. ($e_{294}$=18.9 mM$^{-1}$ cm$^{-1}$).

The GARFT inhibition constant ($K_i$) was determined from the dependence of the steady-state catalytic rate on inhibitor and substrate concentration. The type of inhibition observed was determined to be competitive with respect to FDDF by the dependence of the apparent $K_i$ ($K_{i,app}$) on the concentration of FDDF and was shown to be described by $K_{iapp}=K_i+(K_1/K_m)$ [FDDF]. The Michaelis constant for FDDF, $K_m$, was determined independently by the dependence of the catalytic rate on FDDF concentration. Data for both the $K_m$ and $K_i$ determinations were fitted by nonlinear methods to the Michaelis equation, or the Michaelis equation for competitive inhibition, as appropriate. Data resulting from tight-binding inhibition was analyzed, and $K_i$ determined, by fitting the data to the tight-binding equation of Morrison, Biochem Biophys Acta 185 (1969), 269–286, by nonlinear methods.

Cell lines:

The cell lines used and their origin are tabulated in Table 2. The growth conditions and media requirements of each cell line are summarized in Table 3. All cultures were maintained at 37° C., 5% air-CO$_2$ in a humidified incubator.

In vitro growth inhibition:

Stock solutions of the inhibitors were prepared in 10 mM sodium bicarbonate in water and stored in 1 ml aliquots at −20° C. for cell culture experiments. Cell growth inhibition was measured by a modification of the method of Mosmann, J. Immunol. Methods 65 (1983), 55–63.

Mid-log phase cells of each cell line were diluted to 18,500 cells/ml in fresh RPMI growth medium (Mediatech, Washington, D.C.) supplemented with dialyzed fetal calf serum (Hyclone Laboratories Inc., Logan, Utah) and then aliquotted into columns 2 through 12 of 96-well microtiter plates. Column 1 was filled with the same volume (135 ml) of fresh medium, without cells, for use as a blank. The plates were then placed in a 37° C., 5% air-CO$_2$ incubator. After 1 to 4 hours, plates were removed from the incubator followed by addition of Compound (21) at 10×final concentration, 15 ml/well in binary dilutions, to columns 12 to 4. For reversal experiments, hypoxanthine (1.75 mM) or AICA (1.75 mM) was included in all drug solutions (final concentration 175 mM). Wells containing each concentration of Compound (21) were prepared in quadruplicate on each plate. Fifteen milliliters of media, without Compound (21), were added to the wells in column 1 of the plates. The cells were then returned to the incubator and remained undisturbed for the full incubation period. On day 3 for L1210 and Li210/CI920 cells, or day 5 for CCRF-CEM cells, 50 ml of 0.8 mg/ml MTT ((4,5-dimethylthiazol-2-yl)-2,5-diphenyl tetrazolium bromide; Sigma catalog no. M2128) dissolved in tissue culture medium was added to each well of all plates, after which the cells were returned to the incubator. After 4 hours, all plates were removed from the incubator and centrifuged at 1200 rpm for 7 minutes. Media were siphoned off, and 150 ml of DMSO was added to each well of all plates. Plates were then mixed at slow speed on a vortex mixer for one hour in the dark at room temperature. The extent of metabolized MTT was measured spectrophotometrically at 540 nm on a Molecular Devices Vmax™ kinetic microplate reader. The concentration of drug required to reduce cell growth by 50% as measured by MTT metabolism was determined by interpolation between the O.D. (minus blank) immediately above and below 50% of control O.D. (minus blank).

TABLE 2

| Tissue of Origin and Source of Cell Lines Employed in In Vitro Studies | | |
|---|---|---|
| Cell Line | Source | Origin |
| L1210 | ATCC# | Mouse, lymphocytic leukemia |
| CCRF-CEM | ATCC# | Human, acute lymphoblastic leukemia |

ATCC = American Type Culture Collection

TABLE 3

| Culture Conditions, Plating Densities and Incubation Times Used in Microtiter Assays | | | |
|---|---|---|---|
| Cell line | Medium | DFCS Conc.* (%) | Plating Density (cells/well) | Incubation Time (days) |
| L1210 | RPMI-1640 | 5 | 2500 | 3 |
| CCRF-CEM | RPMI-1640 | 10 | 2500 | 5 |

*DFCS Conc. = dialyzed fetal calf serum concentration.

TABLE 4

Data for Compound 21
Growth Inhibition Using Continuous (72-hour) Exposure

| Compound | GARFT $K_i$ (nM) | $IC_{50}$ Cell Culture L1210 (nM)[a] | $IC_{50}$ Cell Culture CCRF-CEM (nM)[a] |
| --- | --- | --- | --- |
| 21 | 4.5 | 16 | 4.3 |

[a]: Mean $IC_{50}$ ± standard deviation.

In Vivo Antitumor Activity:

On day zero, 2 mm² trocar fragments of 6C3HED lymphosarcoma were implanted subcutaneously in the axillary region into groups of six C3H/He female mice. Starting on day 1, the test compound was administered intraperitoneally in 40% Encapsin given once daily for nine days. Control animals received identical treatment without test compound. The percentage inhibition given in Table 5 below was calculated by comparing the mass of the control tumors (receiving diluent only) on day 11 to those of animals receiving test compound.

TABLE 5

| Compound | Dose (mg/kg) | % Inhibition | Survivors |
| --- | --- | --- | --- |
| 21 | 12.5 | 100 | 6/6 |
| 21 | 25 | 100 | 3/6 |
| 21 | 50 | toxic | 0/6 |

On day zero, 2 mm² trocar fragments of C3H/BA mammary adenocarcinoma were implanted subcutaneously in the axillary region into groups of six C3H/He female mice. Starting on day 1, the test compound was administered intraperitoneally in 40% Encapsin given once daily for nine days. Control animals received identical treatment without test compound. The percentage of inhibition was calculated by comparing the mass of the control tumors (receiving diluent only) on day 14 to those of animals receiving test compound. The results are summarized in Table 6.

TABLE 6

| Compound | Dose (mg/kg) | % Inhibition | Survivors |
| --- | --- | --- | --- |
| 21 | 5 | 16 | 5/6 |
| 21 | 10 | 84 | 6/6 |
| 21 | 20 | 100 | 3/6 |

The compounds and intermediates of the invention contain one or more chiral centers. The invention encompasses racemic mixtures, mixtures of diastereomers, and optically active compounds, such as compounds essentially free of other optical isomers, which optically active compounds can be obtained by means well known to those skilled in the art.

It will be apparent to those skilled in the art that various modifications and variations can be made in the processes and products of the present invention. For example, where possible as a matter of chemistry, chemical groups identified above can be appropriately substituted. In some cases, possible substituents have been explicitly noted. Where more than one $R_6$ group is included in a formula described above, each $R_6$ can be independently selected from the possibilities given.

We claim:

1. A compound of the formula XXI":

wherein:

A is oxygen, sulfur or selenium;

X' is a substituted or unsubstituted $C_1$-$C_3$ alkyl group, a substituted or unsubstituted $C_2$-$C_3$ alkenyl group, a substituted or unsubstituted $C_2$-$C_3$ alkynyl group, a substituted or unsubstituted amino group, sulfur or oxygen;

Y is oxygen, sulfur or NH;

B is hydrogen or a halogen;

C is hydrogen, a halogen or a substituted or unsubstituted $C_1$-$C_6$ alkyl group; and $R_6$ is a hydrogen or a moiety that forms with the attached $CO_2$ a readily hydrolyzable ester group.

2. A compound according to claim 1, wherein: A is sulfur; X' is $CH_2$; Y is sulfur; B is hydrogen; C is hydrogen; and $R_6$ is hydrogen, $C_1$-$C_6$ alkyl, hydroxyalkyl, alkylaryl or arylalkyl.

3. A compound according to claim 1 that is methyl-[2-(2-amino-4-oxo-4,6,7,8-tetrahydro-3H -pyrimido[5,4-6][1,4]thiazin-6-yl)-ethyl]-2,5-thienoate.

4. A compound of the formula XXII":

wherein:

A is oxygen, sulfur or selenium;

X' is a substituted or unsubstituted $C_1$-$C_3$ alkyl group, a substituted or unsubstituted $C_2$-$C_3$ alkenyl group, a substituted or unsubstituted $C_2$-$C_3$ alkynyl group, a substituted or unsubstituted amino group, sulfur or oxygen;

Y is oxygen, sulfur or

B is hydrogen or a halogen; and

C is hydrogen, a halogen or a substituted or unsubstituted $C_1$-$C_6$ alkyl group.

5. A compound according to claim 4, wherein: A is sulfur; X' is $CH_2$; and Y is sulfur.

6. A compound according to claim 4 that is [2-(2-amino-4-oxo-4,6,7,8-tetrahydro-3H-pyrimido[5,4-6]-[1,4]thiazin-6-yl)-ethyl]-2,5-thienoic acid.

7. A compound according to claim 1, wherein the compound of formula XXI" is optically active.

8. A compound according to claim 4, wherein the compound of formula XXII" is optically active.

* * * * *

UNITED STATES PATENT AND TRADEMARK OFFICE
CERTIFICATE OF CORRECTION

PATENT NO. : 5,625,061
DATED : April 29, 1997
INVENTOR(S) : Michael D. VARNEY et al.

It is certified that error appears in the above-indentified patent and that said Letters Patent is hereby corrected as shown below:

ON THE TITLE PAGE

Item [56], under "OTHER PUBLICATIONS," page 2, line 4, "Feb. 5" should read --Feb. 15--;

insert the following under "OTHER PUBLICATIONS": --Totani et al., "Synthesis of a Novel 5-Deaza-5-thia Analogue of Tetrahydrofolic Acid...," J. Chem. Soc. Perkin Trans. 1 (April 1994), 833-836.--

Col. 3, line 50, "monocyclid" should read --monocyclic--.
Col. 4, line 28, "$R_2$is" should read --$R_2$ is--.
Col. 6, line 45, the word "Finally" should begin a new paragraph.
Col. 12, line 12, "CH2" should read --$CH_2$--;
   lines 29, 30, 44, and 45, C2-$C_3$" should read --$C_2$-$C_3$--.
Col. 15, line 46, "includes" should read --include--.
Col. 17, line 16, "pressured" should read --pressure--.
Col. 18, line 55, "(s,3H),," should read --(s,3H),--.
Col. 19, line 24, "(MgS04)" should read --$(MgSO_4)$--;
   line 63, "(MgS04)" should read --$(MgSO_4)$--.
Col. 20, line 39, "Hz," should read --Hz),--.
Col. 21, line 25, "0..586" should read --0.586--.
Col. 22, line 34, "(g,2H,J" should read --(q,2H,J--;

UNITED STATES PATENT AND TRADEMARK OFFICE
CERTIFICATE OF CORRECTION

PATENT NO. : 5,625,061

DATED : April 29, 1997

INVENTOR(S) : Michael D. VARNEY et al.

It is certified that error appears in the above-indentified patent and that said Letters Patent is hereby corrected as shown below:

Col. 22, line 51, "flutamate" should read --glutamate--.
Col. 25, line 26, "(s,3H),," should read --(s,3H),--.
Col. 26, line 17, "1130 cm" should read --1130 cm$^{-1}$--;
  line 62, "StOAc" should read --EtOAc--.
Col. 27, line 52, "mmmol" should read --mmol--.
Col. 28, line 1, "$c_{20}H_{29}NO_8S_2$" should read --$C_{20}H_{29}NO_8S_2$--.
Col. 31, line 24, "Spec" should read --Spec.--;
  line 46, "($K_1/K_m$)" should read --($K_i/K_m$)--.
Col. 32, line 27, "Li210/CI920" should read --L1210/CI920--.
Col. 33, lines 18-19, "test: compound" should read --test compound--.

IN THE CLAIMS

Claim 4, col. 34, line 54, "sulfur or" should read --sulfur or NH;--.

Signed and Sealed this

Fourteenth Day of October, 1997

Attest:

BRUCE LEHMAN

Attesting Officer

Commissioner of Patents and Trademarks